US012636189B2

(12) United States Patent
Lobanoff

(10) Patent No.: US 12,636,189 B2
(45) Date of Patent: *May 26, 2026

(54) INTELLIGENT CORNEAL PROCEDURE ADVISOR

(71) Applicant: ALCON INC., Fribourg (CH)

(72) Inventor: Mark Lobanoff, North Oaks, MN (US)

(73) Assignee: ALCON INC., Fribourg (CH)

( * ) Notice: Subject to any disclaimer, the term of this patent is extended or adjusted under 35 U.S.C. 154(b) by 358 days.

This patent is subject to a terminal disclaimer.

(21) Appl. No.: 18/223,397

(22) Filed: Jul. 18, 2023

(65) Prior Publication Data

US 2024/0082059 A1        Mar. 14, 2024

Related U.S. Application Data

(63) Continuation of application No. 16/800,580, filed on Feb. 25, 2020, now Pat. No. 11,701,258, which is a
(Continued)

(51) Int. Cl.
*A61F 9/008* (2006.01)
*G06T 7/00* (2017.01)
(Continued)

(52) U.S. Cl.
CPC .......... *A61F 9/008* (2013.01); *A61F 9/00804* (2013.01); *G06T 7/0012* (2013.01); *G06T 7/60* (2013.01); *G16H 20/30* (2018.01); *G16H 30/40* (2018.01); *G16H 50/20* (2018.01); *G16H 50/70* (2018.01); *A61B 2017/00221* (2013.01);
(Continued)

(58) Field of Classification Search
None
See application file for complete search history.

(56) References Cited

U.S. PATENT DOCUMENTS

2003/0128334 A1* 7/2003 O'Donnell, Jr. .... A61F 9/00804
606/5

FOREIGN PATENT DOCUMENTS

WO        WO-2017091200 A1 *   6/2017   ......... A61F 9/00806

* cited by examiner

*Primary Examiner* — Michael T. Holtzclaw

(57) ABSTRACT

Generation of treatment recommendations for topographic-based excimer laser surgical procedures is described that includes generating accurate cylinder compensation and spherical compensation values that are adjusted to compensate for unique characteristics of topographic-based excimer laser surgical systems. Generating treatment recommendations generally includes determining a topographic vector, a posterior astigmatism vector and an anterior astigmatism vector, and generating an internal astigmatism vector using the topographic vector, the posterior astigmatism vector, the anterior astigmatism vector, and a manifest astigmatism vector. In embodiments, the cylinder compensation is generated using multiple vectors while subtracting the internal astigmatism vector and the posterior astigmatism vector which remain in the eye after treatment, and the spherical compensation is generated using an initial spherical compensation modified by addback modifiers and a regression analysis nomogram. In procedures where the corneal epithelium is removed, an epithelial refractive vector is determined from an epithelial thickness/topography map and added to the other vectors.

20 Claims, 16 Drawing Sheets

Related U.S. Application Data continuation-in-part of application No. 16/523,198, filed on Jul. 26, 2019, now Pat. No. 11,638,661.

(60) Provisional application No. 62/798,162, filed on Jan. 29, 2019, provisional application No. 62/770,045, filed on Nov. 20, 2018.

(51) Int. Cl.

| | |
|---|---|
| *G06T 7/60* | (2017.01) |
| *G16H 20/30* | (2018.01) |
| *G16H 30/40* | (2018.01) |
| *G16H 50/20* | (2018.01) |
| *G16H 50/70* | (2018.01) |
| *A61B 17/00* | (2006.01) |

(52) U.S. Cl.

CPC ............... *A61F 2009/00851* (2013.01); *A61F 2009/00872* (2013.01); *A61F 2009/00878* (2013.01); *A61F 2009/0088* (2013.01); *A61F 2009/00882* (2013.01); *G06T 2207/30041* (2013.01)

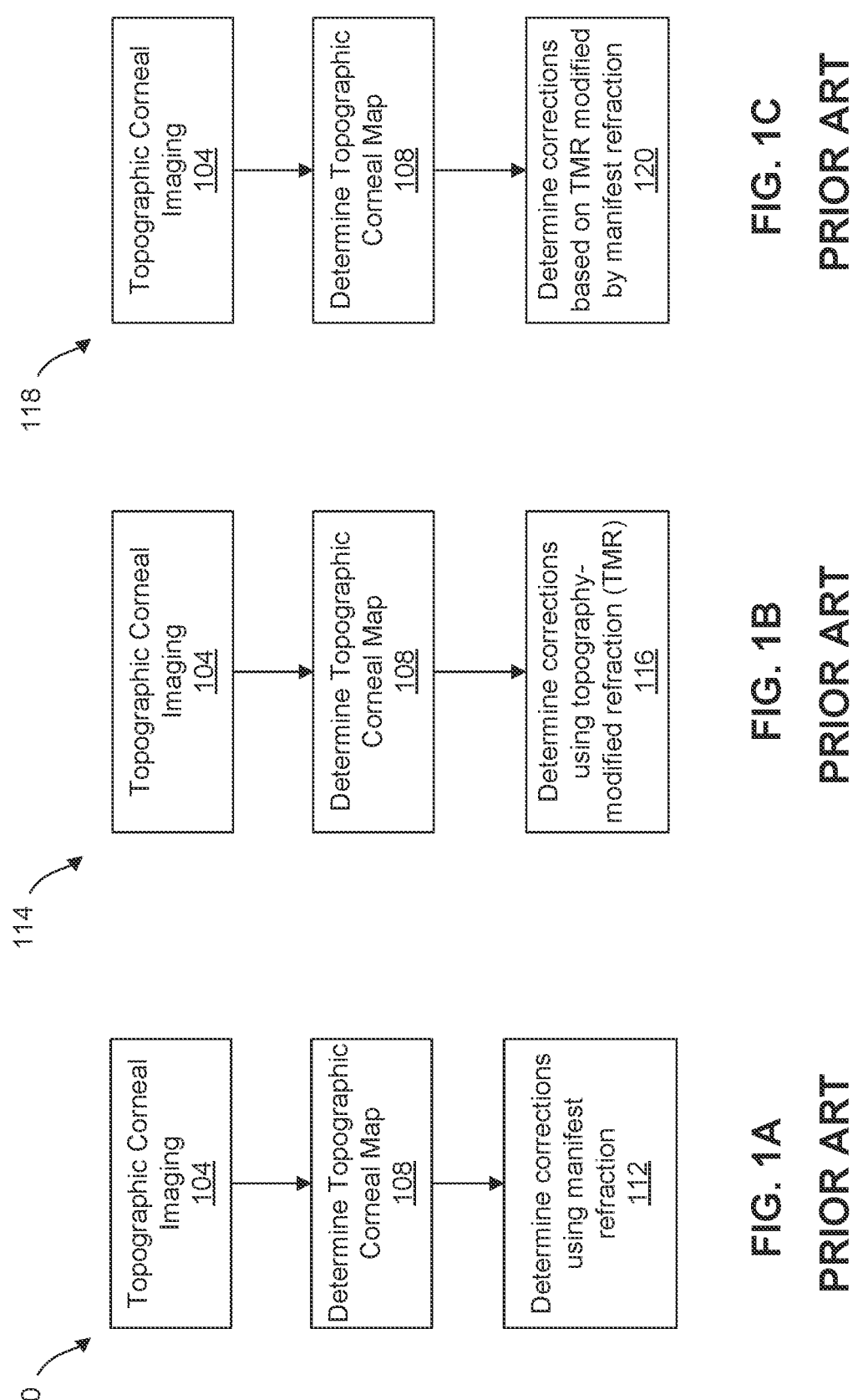

Topographic Corneal Imaging 104

Determine Topographic Corneal Map 108

Determine corrections based on TMR modified by manifest refraction 120

FIG. 1C
PRIOR ART

Topographic Corneal Imaging 104

Determine Topographic Corneal Map 108

Determine corrections using topography-modified refraction (TMR) 116

FIG. 1B
PRIOR ART

Topographic Corneal Imaging 104

Determine Topographic Corneal Map 108

Determine corrections using manifest refraction 112

INTELLIGENT CORNEAL PROCEDURE ADVISOR

CROSS REFERENCE TO RELATED APPLICATIONS

This application is a Continuation of application Ser. No. 16/800,580 filed Feb. 25, 2020, which is a CIP of application Ser. No. 16/523,198, filed Jul. 26, 2019, which claims benefit of Application No. 62,770,05, filed Nov. 20, 2018 and claims benefit of Application No. 62,798,162, filed Jan. 29, 2019, the disclosures of which are incorporated by reference herein in its entirety.

FIELD OF THE DISCLOSURE

The present disclosure relates to excimer laser refractive surgery, and more specifically, to intelligent advisor systems for assisting practitioners in excimer laser refractive surgery.

BACKGROUND

Laser-assisted in situ keratomileusis (LASIK) has become one of the most widely used forms of excimer laser refractive surgery today. Generally, the objective of this surgical technique is to modify a patient's anterior corneal shape by ablating tissue to precisely change the shape of the cornea. Since the surface of the cornea and its air-tear interface are responsible for majority the refractive power of the eye, by reshaping the cornea various corrections can be made to reduce or even eliminate common vision issues such as nearsightedness (myopia), farsightedness (hyperopia), and astigmatism.

For instance, in LASIK procedures for myopia, stromal tissue is removed so that the curvature of the central cornea is flattened to compensate for the excessive refractive power or longer axial length of the myopic eye. In hyperopic LASIK, to steepen an untreated central cornea, a relatively deep peripheral corneal ablation can be performed to compensate for the insufficient refractive power or shorter axial length of the hyperopic eye.

In preparation, a practitioner will initially need to measure the cornea to evaluate which areas and to what extent the cornea requires reshaping. As such, a practitioner can make various measurements noting the shape, contour, thickness and any corneal irregularities. Further, the type and extent of corneal measurements will be made based on the type of refractive surgery being performed. For instance, types of excimer laser refractive surgery can include wavefront-guided applications or topographic-guided applications.

In wavefront-guided applications, treatments are generally based on measurements of the total optical system (e.g. tear film, anterior corneal surface, corneal stroma, posterior corneal surface, crystalline lens, vitreous and retina). In such applications, measurements can be converted into mathematical data, such as Zernike polynomials, that are used to classify/quantify corneal aberrations and to determine an ablation profile.

In topographic-guided applications, treatments are generally based on measurements of the cornea to develop a corneal topography that identifies various topographic features/irregularities. In such applications, a desired corneal surface is additionally determined with the goal of correcting the refractive error and detected aberrations. The difference between the measured corneal topography and the desired surface is used to determine an ablation profile.

Development of topography-guided custom ablations enables practitioners to perform individualized treatments precisely controlled by size, depth and location. As such, corneal topography-guided ablation has significant potential benefits in patients with relatively large contour abnormalities such as regular and irregular astigmatism, decentered ablations and central islands. In addition, topography-guided applications allow for additional advancements, including Q-factor adjusted treatments to preserve corneal tissue and/or optimize asphericity of the cornea.

However, the results of wavefront-guided applications or topographic-guided applications of excimer laser refractive surgery are not always ideal. For instance, patients can experience a variety of potential complications, including astigmatism, glare, halos, double-vision, or issues arising from under-corrections or overcorrections during the surgical process.

As a result, improvements to excimer laser refractive surgery applications would be welcome.

SUMMARY

Various embodiments of the disclosure are directed to systems, methods, and computer program product for an intelligent advisor for corneal surgical procedures. In particular, various embodiments are directed to an intelligent advisor system configured to provide treatment recommendations for topographic-guided applications of excimer laser refractive surgery.

In various embodiments, topographic-guided applications of excimer laser refractive surgery utilize computer-assisted diagnostic tools to create a three-dimensional map of the surface curvature of the cornea. For instance, after measuring the features of a cornea, computer software digitizes collected data points to produce a printout of the corneal shape. In certain instances, this can include using different colors to identify different elevations, much like how a topographic map of the earth displays changes in the land surface. As a result, corneal topography produces a detailed, visual description of the specific shape/features of the cornea. For laser vision correction, this corneal topography map can be used to determine how much corneal tissue will be removed, and with what ablation pattern, to improve a patient's vision.

This type of analysis provides fine details regarding the condition of the corneal surface and is particularly useful for identifying and treating astigmatism where the corneal surface is irregularly or unevenly shaped. This allows a practitioner to diagnose, monitor, and treat various eye conditions or detect other conditions that would be invisible to wavefront-guided applications or other conventional tests.

In addition, in various embodiments, topographic-guided applications of excimer laser refractive surgery can utilize computer-assisted diagnostic tools to create a map of the thickness of the corneal epithelium. For instance, after measuring the features of a corneal epithelium, computer software digitizes collected data points to produce a printout of the regional variances in the epithelial thickness. As a result, corneal epithelium topography produces a detailed, visual description of the specific shape/features of the epithelium.

Topographic-guided applications of excimer laser refractive surgery generally treat corneas differently than other forms of excimer laser refractive surgery—by correcting specific topographical irregularities detected on the corneal surface. However, these topographic irregularities have an optical effect and contribute to a patient's overall manifest refraction. For instance, as the visual system develops, the brain begins dealing with some aberrations as complementary aberrations and uses them to improve vision while other aberrations diminish or reduce a patient's vision. As a result, while some spherical aberrations may function to diminish a patient's functional vision other spherical aberrations may improve the quality of vision. For example, in one patient, a specific spherical aberration may function to improve the patient's vision while the same or similar spherical aberration functions to diminish a different patient's functional vision. Traditional excimer laser refractive surgery instruments/methods do not discriminate which aberrations are beneficial and which are harmful to vision.

Furthermore, specific features/measurements of the cornea are often dependent with one another—and corrections to aberrations to the corneal surface can in turn affect cylinder, sphere, and other portions of the cornea in ways that can negatively affect the patient's vision or reduce the resulting improvement from correction.

In addition, traditional excimer laser refractive surgery instruments do not account for differences in refractive properties of the epithelium before or after surgery, which may present a significant optical effect at least from thickness variations of the epithelium resulting from the uneven corneal tissue underneath and when compared to a more uniform epithelium thickness in a normal cornea or when the epithelium is regrown after some procedures.

As a result, while traditional methods can treat or remove spherical aberrations, they do necessarily produce optimal improvements to a patient's vision, as the optical effect those treatments will have on a patient's vision are not taken into account or predicted in advance. For instance, existing methods for treatment have attempted to utilize the patent's manifest refraction, in conjunction with the corneal topography map, to determine the accuracy of the detected aberrometry and/or to modify laser treatments. This subjective measure facilitates a comparison between the patient's cortical adaptation to their aberrations and the absolute quantitative levels the identified aberrations For example, referring to FIG. 1A, a known method 100 is depicted where imaging 104 and topographic mapping 108 are performed. Treatments are then made using manifest refraction to determine the accuracy of the detected aberrometry and/or to modify laser treatments at operation 112. However, results using this method 100 have been unsatisfactory, as the treated topographic irregularities have an optical effect that cannot be predicted simply using the manifest. This made resulting vision improvements for patients inconsistent.

As another example, an effort was taken in topographic-guided applications to treat completely off of the measured anterior corneal astigmatism magnitude and axis, the topography-modified refraction (TMR). For instance, FIG. 1B depicts a known method 114 where imaging 104 and topographic mapping 108 are performed. Treatments are then made using the TMR, at operation 116. This insight led practitioners to realize the importance of correcting the complete anterior corneal measured astigmatism if you are to correct the anterior corneal topographic irregularities as well. The results of TMR were better than treating off of the manifest refraction. However, there were cases in which treating the full TMR led to the astigmatic axis being flipped after surgery. In other cases, residual astigmatism remained that kept patients from their best vision.

Seeing the results of TMR, some practitioners began to treat 50% of the difference between the manifest and the measured astigmatism. For example, FIG. 1C depicts a known method 118 where imaging 104 and topographic mapping 108 are performed, with treatments made using the TMR modified by manifest refraction, at operation 120. This technique was appealing in its simplicity and being conservative, it would not result in a flipped axis in most cases. However, this technique is at its heart a guess at what the best astigmatic axis and magnitude should be.

By ignoring the refractive effect of eliminating the topographic irregularities, practitioners were not achieving patient visual acuity results as good as they would want. For example, if the topographic irregularities were large, the astigmatic axis resulting from the treatment methods in FIGS. 1A-1C could result in large errors.

As such, one or more embodiments of the disclosure provide an improved approach to known methods—providing an intelligent advisor system for topographic-guided applications of excimer laser refractive surgery that utilizes analysis based on mathematical/optical physics principles to produce a surgical treatment recommendation that assists surgeons in making treatment decisions.

In one or more embodiments, an intelligent advisor system is disclosed for generating a treatment recommendation for a corneal surgical procedure on an eye, the treatment recommendation including a cylinder compensation and a spherical compensation. In various embodiments, the system includes a processor and a computer readable storage medium having program instructions embodied therewith, wherein the computer readable storage medium is not a transitory signal per se. In one or more embodiments, the program instructions are executable by the processor to cause the processor to determine a topographic vector from a topographic corneal map of the eye, the topographic vector indicating a magnitude and a direction of an optical effect of a corneal talus, and determine a posterior astigmatism vector and an anterior astigmatism vector for the eye.

In one or more embodiments, the program instructions are executable by the processor to cause the processor to generate an interior astigmatism vector using the topographic vector, the posterior astigmatism vector, the anterior astigmatism vector, and a manifest astigmatism vector, and to generate the cylinder compensation of the treatment recommendation using the interior astigmatism vector and the posterior astigmatism vector. In various embodiments, the program instructions are executable by the processor to cause the processor to generate the spherical compensation of the treatment recommendation using an initial spherical compensation modified by a topographic addback modifier and a cylinder addback modifier, where the topographic addback modifier is a value indicating a refractive effect of a difference between a height of a highest talus and an amount of tissue removed from the center of the cornea, and where the cylinder addback modifier is a value of one half a difference between a magnitude of the manifest astigmatism vector and the magnitude of the corneal cylinder to be treated by the laser. In various embodiments, the program instructions are executable by the processor to cause the processor to indicate the treatment recommendation including the cylinder compensation and the sphere compensation to a user.

In one or more embodiments the topographic corneal map, the posterior astigmatism vector, the anterior astigmatism vector, and the initial spherical compensation are received as a plurality of inputs from an external system. In such embodiments, the plurality of inputs can be generated using Contoura® topography guided LASIK software or other suitable LASIK software system. In various embodiments, the corneal surgical procedure is a topographic-based excimer laser surgical procedure, however, in certain embodiments, the corneal surgical procedure is one or more of a PRK surgery, a SMILE surgery, astigmatic incisions, and astigmatism management for cataract surgery.

In addition, various embodiments of the disclosure contemplate that additional sets of vectors can be used to further optimize a treatment plan. In some embodiments, these additional vectors could be particularly useful for different types of surgical procedures. For example, in some procedures, such as photorefractive keratectomy (PRK) where the epithelium is completely removed and then subsequently regrown after treatment, the pre-surgery epithelium may have one or more epithelial "taluses" that indicate a thicker or thinner portion of the epithelium that corresponds to uneven shape of the cornea. In such embodiments, the amount of corneal tissue removed and the associated ablation pattern should be additionally adjusted at least based on the corneal epithelium thickness map to achieve best results.

As such, in one or more embodiments, the program instructions are executable by the processor to cause the processor to determine an epithelial refractive vector from a topographic or thickness epithelial map of the eye, the epithelial vector indicating a magnitude and a direction of an optical effect of an epithelial talus (talus defined here as an area of epithelium that is thicker or thinner than the human normal value of 50 microns). Accordingly, a treatment plan can be determined that accounts for the optical effects of removing an epithelium having variable thickness and regrowth of a new epithelium having a generally uniform thickness.

The above summary is not intended to describe each illustrated embodiment or every implementation of the present disclosure.

BRIEF DESCRIPTION OF THE SEVERAL VIEWS OF THE DRAWINGS

The drawings included in the present application are incorporated into, and form part of, the specification. They illustrate embodiments of the present disclosure and, along with the description, serve to explain the principles of the disclosure. The drawings are only illustrative of certain embodiments and do not limit the disclosure.

FIGS. 1A-1C depict known methods for excimer laser refractive treatments.

Figure 2:
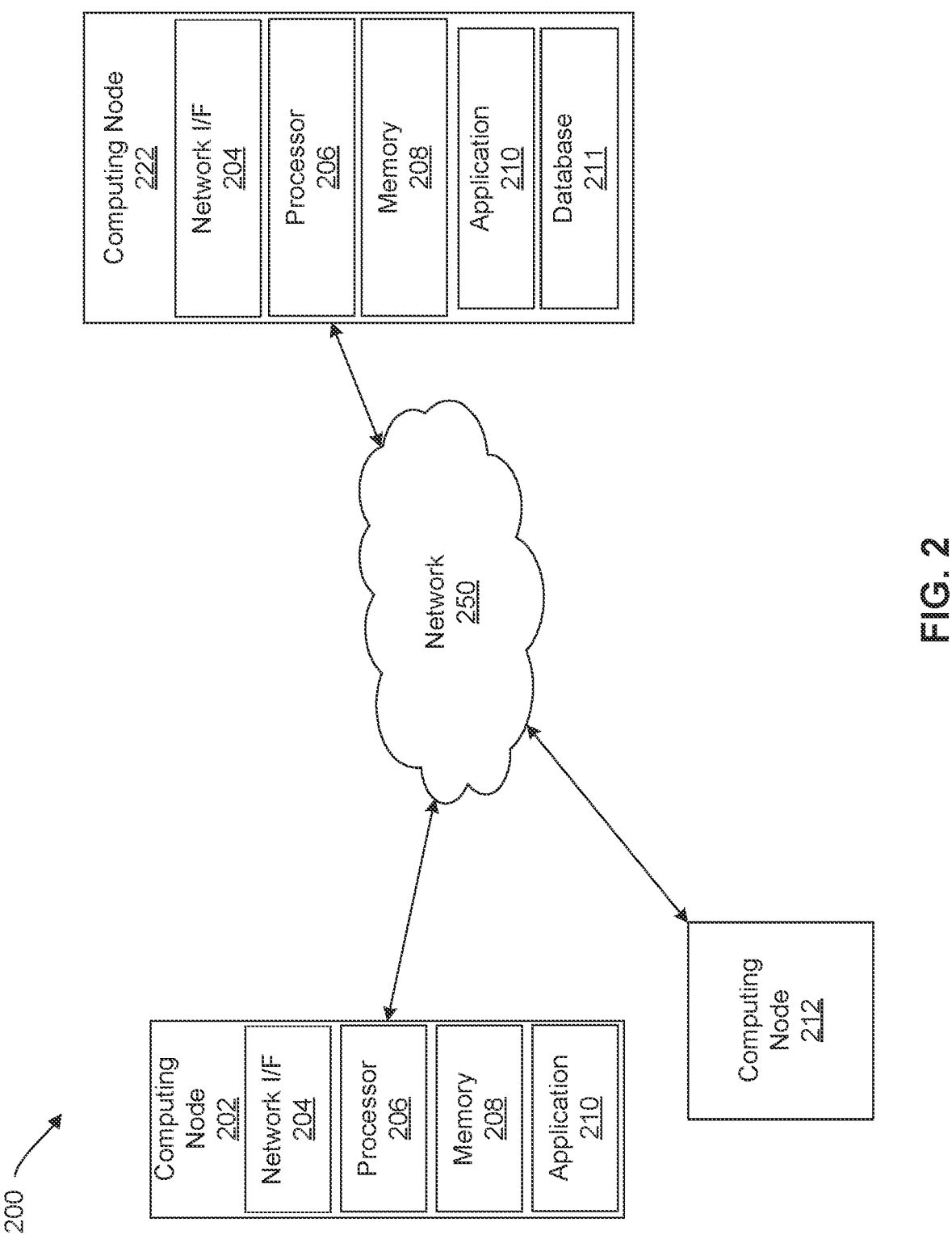
FIG. 2 depicts a block diagram of an example computing environment for use with an intelligent advisor system, according to one or more embodiments of the present disclosure.

While the embodiments of the disclosure are amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DETAILED DESCRIPTION

Referring to FIG. 2 a block diagram of an example computing environment 200 for use with an intelligent advisor system can be seen, according to one or more embodiments of the present disclosure. In some embodiments, the computing environment 200 can include one or more computing nodes 202, 212, and 222. Computing nodes of the computing environment may be physical devices, usable by a consumer or other user, including processing elements and memory. In some embodiments, the computing nodes include, for example, a desktop computer, laptop computer, tablet device, smart phones, wearable computing device, or other suitable device.

Consistent with various embodiments, computing nodes 202, 212, 222 can be computer systems, and can each be equipped with a display or monitor. In various embodiments these computer systems include a processor 206, 216, 226; memory 208, 218, 228; internal or external network interface or communications devices 204, 214, 224 (e.g., modem, network interface cards); optional input devices (e.g., a keyboard, mouse, touchscreen, or other input device); and commercially available or custom software (e.g., a graphical user interface (GUI) for receiving commands and outputting data to users, browser software, communications software, server software, natural language processing software, search engine and/or web crawling software, filter modules for filtering content based upon predefined criteria).

Seen in FIG. 2, the computing nodes are interconnected via a network 250, for communication. As such, in various embodiments the computing nodes 202, 212 could be remote devices positioned distant from and networked with computing node 222 configured as a host device—configured to communicate over the network 250. In certain embodiments, the host device can be a central hub from which remote devices establish a communication connection. In some embodiments, the host device and remote devices can be configured in various suitable relationships (e.g., server-client, peer-to-peer, or other suitable relationship).

In one or more embodiments, the network 250 can be implemented by any suitable communications media (e.g., wide area network (WAN), local area network (LAN), Internet, and Intranet). In some embodiments, computing nodes 202, 212, 222 can be local to each other, and communicate via appropriate local communication medium (e.g., local area network (LAN), hardwire, wireless link, Intranet). In certain embodiments, computing nodes 202, 212, 222 are directly connected via a wireless connection or via a wired connection. For example, in certain embodiments a network adapter can communicate using Wi-Fi, BLUETOOTH®, or other suitable type of wireless communication. In some embodiments, computing nodes 202, 212, 222 are directly connected via a wired connection.

In some embodiments, the network 250 can be implemented within a cloud computing environment, or using one or more cloud computing services. Consistent with various embodiments, a cloud computing environment can include a network-based, distributed data processing system that provides one or more cloud computing services. Further, a cloud computing environment can include multiple computers (e.g., hundreds or thousands of them or more), disposed within one or more data centers and configured to share resources over the network 250.

In one or more embodiments, the computing nodes 202, 212, 222 outputs data and receives inputs to/from users. For example, the computing nodes 202, 212, 222 may each include input/output devices, for example a display and/or touchscreen, for interfacing with a user via a graphical user interface (GUI) or other user interface. In one or more embodiments, each of the computing nodes 202, 212, 222 includes application 210 ("App"). In some embodiments, the App 210 is a program or "software" that is stored in memory accessible by computing nodes 202, 212, 222 for execution on the computing nodes 202, 212, 222. In one or more embodiments, App 210 includes a set of instructions for execution by processing elements on one or more of the computing nodes 202, 212, 222, as part of an intelligent advisor system for generating treatment recommendations for topographic-guided applications of excimer laser refractive surgery. In certain embodiments, App 210 is stored locally on some or all of the computing nodes 202, 212, 222. In some embodiments, App 210 is stored remotely, accessible to some or all of the computing nodes 202, 212, 222 via network 250.

In some embodiments, when executing App 210, computing nodes 202, 212, 222, are arranged in a client server architecture. For example, computing node 222 may be configured as a server with computing nodes 202, 212 arranged as clients. For example, depicted in FIG. 2, computing node 222 is a server including database 211, and computing nodes 202, 212 are clients that use App 210 to communicate with the server to input data, access resources at the server, such as processing, memory, or data resources, such as data stored in database 211 In some embodiments, when executing App the computing nodes 202, 212, 222 are arranged in a peer-to-peer architecture, with computing nodes 202, 212, 222 acting as both client and server.

Described further below, in various embodiments App 210 is an application dedicated to intelligent advisor system. As such, in some embodiments, the computing environment is an example of an intelligent advisor system, where one or more of the computing nodes 202, 212, 222 are configured having an input analysis module with an answer generator. The input analysis module can be configured to receive various inputs, such as corneal imaging data—either in real time or stored within one or more databases—and to process said inputs for the answer generator module. In such embodiments, computing nodes 202, 212, 222 enable users to submit input data (e.g., corneal image data or other inputs) to for analysis/processing by app 210. For example, the input analysis module can receive inputs via a graphical user interface or other interface (command line prompts, menu screens, etc.) to solicit data from users for submission to the answer generation module and to display answers/results in relation to such user queries. In various embodiments, the user interface is in the form of a web browser or other suitable software module.

Figure 3:
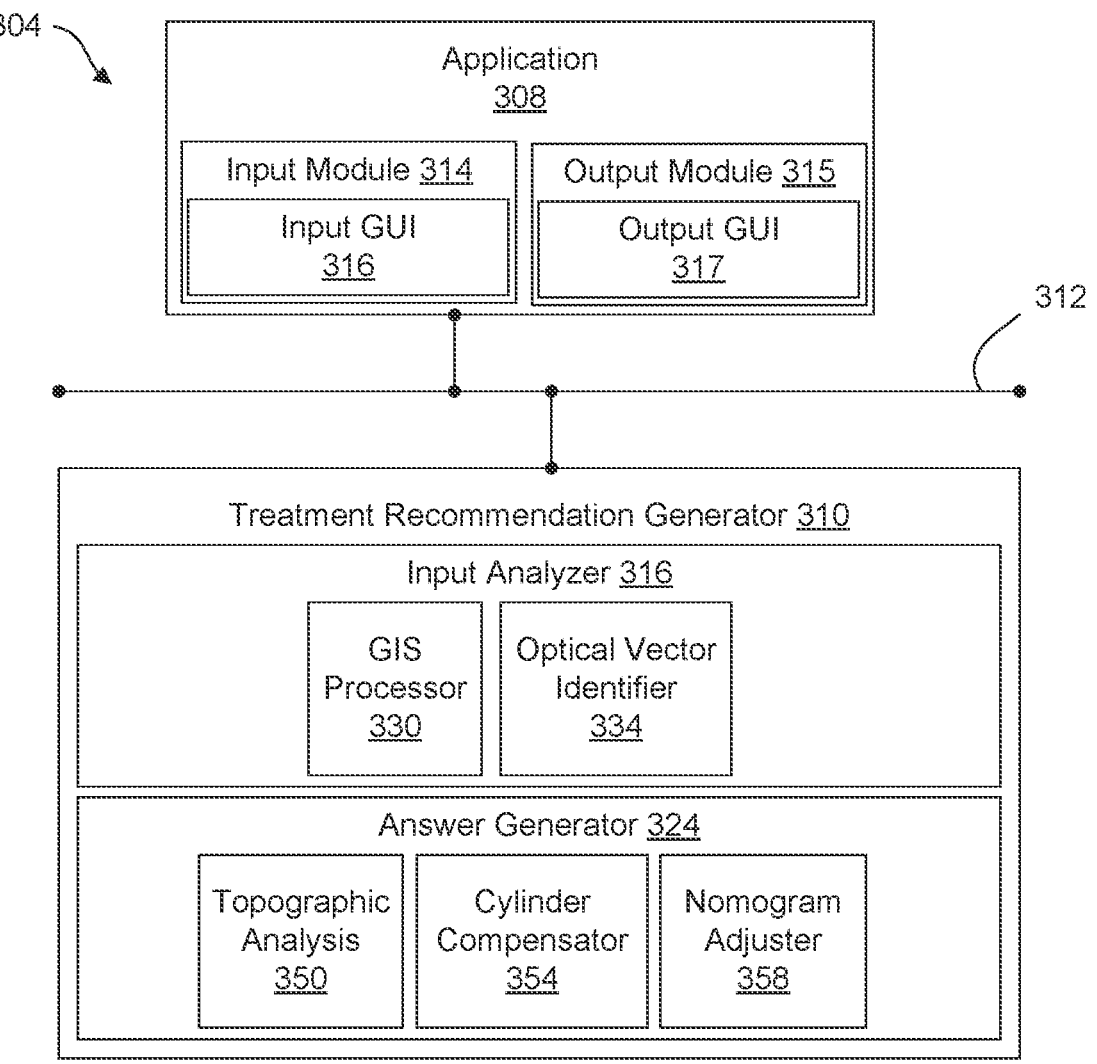
FIG. 3 depicts a block diagram of system architecture including an intelligent advisor system, according to one or more embodiments of the disclosure.

Referring now to FIG. 3 a block diagram of system architecture of an intelligent advisor system 304 can be seen, according to one or more embodiments of the disclosure. The various components of the advisor system 304 described herein can be used to implement various aspects of the present disclosure. For example, in various embodiments, the system 304 is generally configured to receive one or more inputs from a user, analyze said inputs, and to generate an answer for the user in response. As described herein, the answer of the system 304 is generally in the form of a treatment recommendation for topographic-guided applications of excimer laser refractive surgery. In such embodiments, and described further below, the system 304 is then configured to render a visualization of the generated treatment recommendation and to present it to the user as a system output.

As described, in various embodiments the intelligent advisor system 304 includes a plurality of components including a user-facing application 308 and a treatment recommendation generator 310. In various embodiments, the application 308 is a user-facing component of the system 304 that enables users to interact with various elements of the system 304. As such, application 308 is configured to allow for submission of input data (e.g., corneal image data, epithelium image data, or other inputs) for analysis/processing by the treatment recommendation generator 310 and is configured to present output data, such as a treatment recommendation generated by the treatment recommendation generator 310, feedback data, or other data back to the user.

For example, in various embodiments, the application 308 includes an input module 314—referring to a collection of software/executable instructions that are configured to present a user-facing graphical user interface 316 or other interface (command line prompts, menu screens, etc.) to solicit data from users for submission to the answer generation capabilities of the advisor system 304. Similarly, in various embodiments the application 308 includes an output module 315—referring to a collection of software/executable instructions that is configured to present a user-facing graphical user interface 317 or other interface (command line prompts, menu screens, etc.) to present output data, feedback information, or other information for users of the answer generation capabilities of the advisor system 304. As such, the application 308, by receiving inputs via the input module 314 and/or GUI 316, can dispatch user query requests and/or data to the elements of the advisor system 304. Similarly, application 308 can, via the output module 315 and/or GUI 317, can output generated treatment recommendations or other information generated from elements of the advisor system 304.

Consistent with various embodiments, the GUI 316, 317 of input module 314 and output module 315 can include command line prompts, menu screens, or the like to solicit data from users for submission to the answer generation module and to display answers/results in relation to such user queries. In various embodiments, the GUI 316, 317 is in the form of a web browser or other interface. In certain embodiments, GUI 316, 317 could be substantially similar or be included in a common user interface that is configured to both receive inputs and display outputs.

As described above, elements of the QA system 312 can be communicatively coupled through a network 312, e.g., the Internet, intranet, or other public or private computer network. For instance, as depicted in FIG. 2, in various embodiments the application 308 could reside on a first computing node, such as a client node, while the treatment recommendation generator 310 resides on a second computing node, such as a server node. In such embodiments, advisor system 304 and client application 308 can communicate by using Hypertext Transfer Protocol (HTTP), Representational State Transfer (REST) calls, or other suitable networking protocol. In some embodiments, the network 312 can be implemented within a cloud computing environment, or using one or more cloud computing services.

In various embodiments, the treatment recommendation generator 310 includes a collection of software modules/executable instructions that are configured to analyze/processes user inputs for generating a treatment recommendation for topographic-guided applications of excimer laser refractive surgery. In one or more embodiments, the treatment recommendation generator 310 can include an input analyzer module 316 and answer generator module 324.

In various embodiments, the input analyzer 316 is a software module that analyzes the received inputs. As such, in various embodiments, the input analyzer 316 can perform various methods and techniques for analyzing inputs including, but not limited to, image recognition and geographical imaging. As such, in various embodiments the input analyzer 316 can include input analysis elements including a geographical imaging system (GIS) processor 330 and a topographic optical vector identifier 334.

Figure 4A:
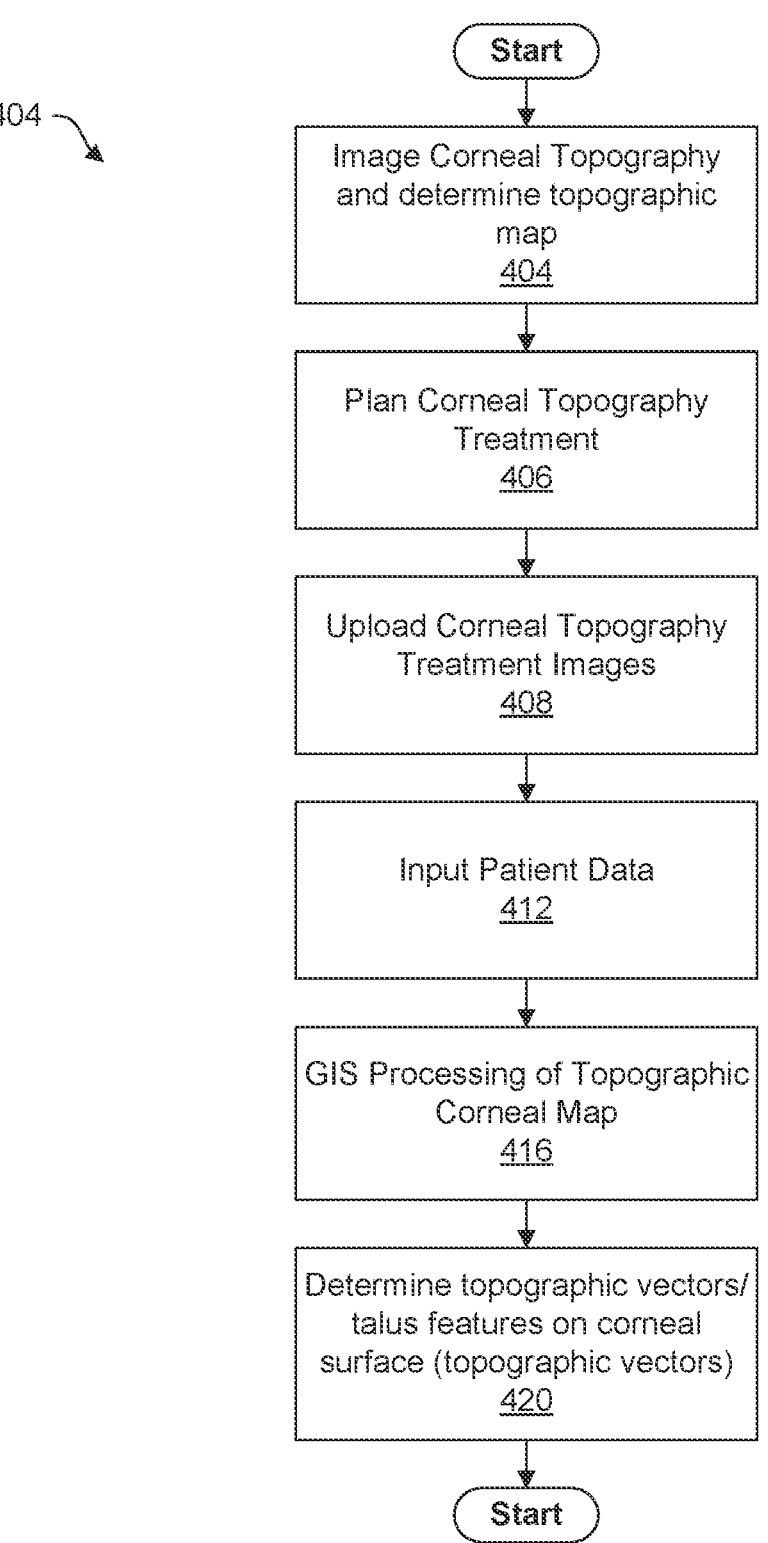
FIG. 4A depicts a flowchart diagram of a method of input analysis for an intelligent advisor system, according to one or more embodiments of the disclosure.
Figure 4B:
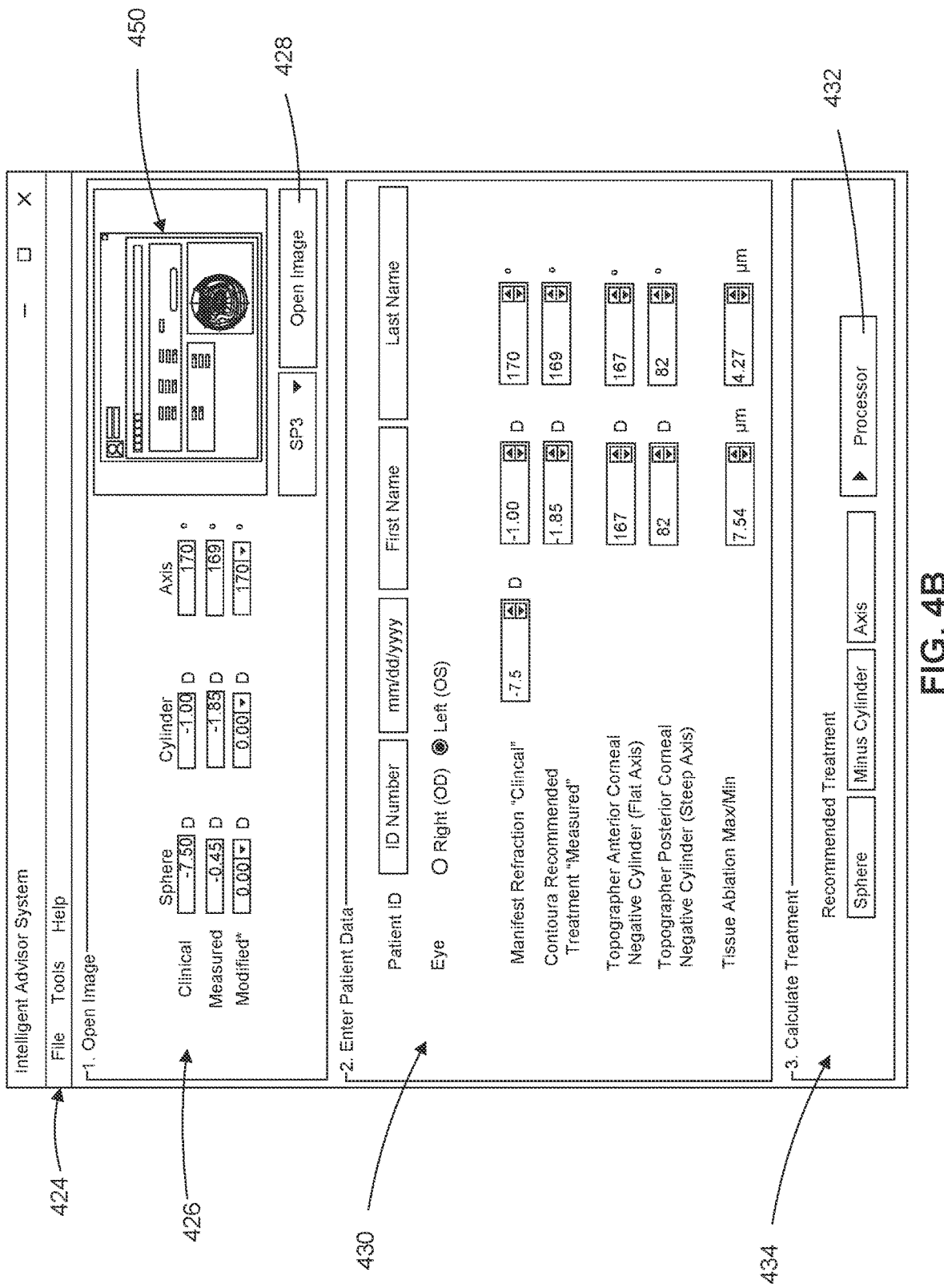
FIG. 4B depicts a GUI element of an input analyzer for an intelligent advisor system are depicted, according to one or more embodiments of the disclosure.

Referring additionally to FIGS. 4A-4B a flowchart diagram of a method 404 of input analysis and an example GUI element 424 of the input analyzer 316 are depicted, according to one or more embodiments of the disclosure. Specifically, in various embodiments, the method 404 depicts a method of operation of the input analyzer 316. As such, in one or more embodiments, and described further below, the method 404 includes various operations that can be elements of a computer program product representation of the input analyzer 316. In such embodiments, the operations of method 404 can be included as executable program instructions that are embodied in a computer readable storage medium. In various embodiments, the method 404 depicts input analyzer means for accomplishing various embodiments of the disclosure. Similarly, the GUI element 424 of FIG. 4B depict a visualization of a computer program product that, when executed by a computer, produces visual representation of the input analyzer 316.

Figure 5A:
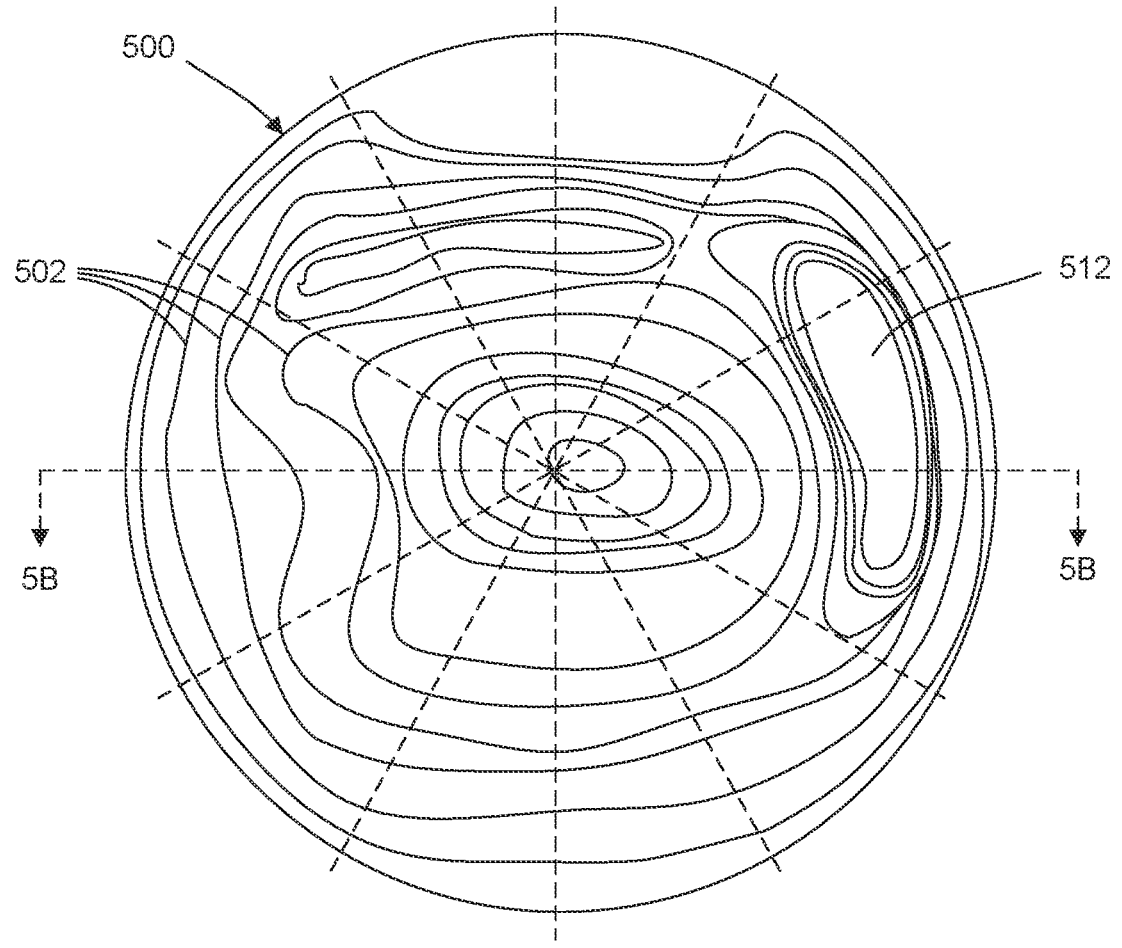
FIG. 5A depicts a topographic map of an imaged cornea, according to one or more embodiments of the disclosure.
Figure 5B:
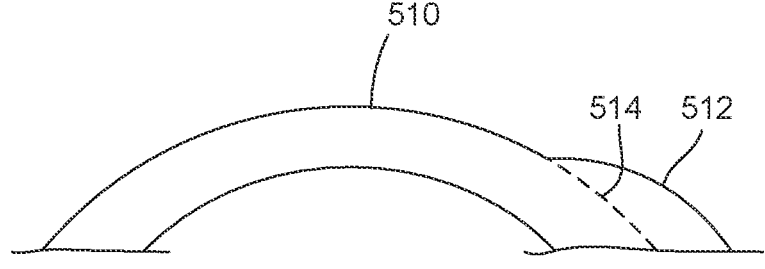
FIG. 5B depicts a partial cross-sectional view of a cornea with a talus, according to one or more embodiments of the disclosure.

In FIG. 4A, in various embodiments, the method 404 includes, at operation 410, imaging a cornea to determine a corneal topographic map. As described above, corneal topography provides a detailed description of various curvature and shape characteristics of the cornea. In particular, various embodiments of corneal topography depict the three-dimensional shape of the cornea's surface with contour lines at specific intervals to depict the shape and elevation (or relief) of the corneal surface. For example, referring to FIGS. 5A-5B, an example topographic image 500 of a cornea and cross-sectional view of a cornea 510 is depicted. As described, the topographic image 500 depicts a three-dimensional corneal surface via a plurality of contour lines 502 that depict a general shape and elevation of the cornea. As described, in various instances, the cornea 510 can include a variety of aberrations, such as an irregular shape from portion of raised material on the corneal surface. In FIGS. 5A-5B, the cornea 510 is depicted with a collection of material formed on the side of the cornea 510 that defines a talus 512 of raised or irregular material, relative to what would normally be present on a normally shaped cornea. This difference is depicted in dashed lines 514 in FIG. 5B which depicts the material that would be present in a normal cornea and demonstrate the extent of excess material that makes up the talus 512. As described above, the talus 512 has an optical effect a patient's overall manifest refraction— potentially diminishing or negatively impacting a patient's vision.

In various embodiments, the corneal topography can by imaged using a variety of known methods for imaging and recording a topographic image of the cornea. For example, in various embodiments topographic images can be obtained via a Pentacam®, Galilei®, or other suitable optical measurement device. These devices use scheimpflug and/or ocular coherence tomography (OCT) but could employ other technologies. Further, while FIG. 5A depicts a topographic map without color, in various embodiments corneal topography maps utilize advanced color scales to identify curvature data. For example, areas of steeper curvature can be displayed in warm colors such as red and orange, whereas areas of flatter curvature are illustrated in cool colors such as green and blue. In various embodiments, the topographic image can be displayed according to "absolute" and/or "normalized" scales, where an absolute scaled image displays a fixed range of curvatures and the normalized scaled image displays a range of curvature or power calculated from the specific image of the cornea.

In various embodiments, the method 404 includes, at operation 406, determining a corneal topography treatment recommendation. In one or more embodiments, the images produced in operation 404 can be analyzed to develop a treatment map. In such embodiments, the treatment map will indicate the position and extent of any corneal aberrations what ablations would be required to correct the corneal shape. As described above, corneal topography treatment recommendation can be determined using one or more of a variety of standard topography based LASIK treatment systems, such as for example via Contoura® topography guided LASIK software or other suitable LASIK software. For example, referring briefly to FIG. 4C, an example treatment recommendation is depicted showing the sphere, cylinder and axis measurements, along with an ablation profile and corneal and ablation details.

Figure 4C:
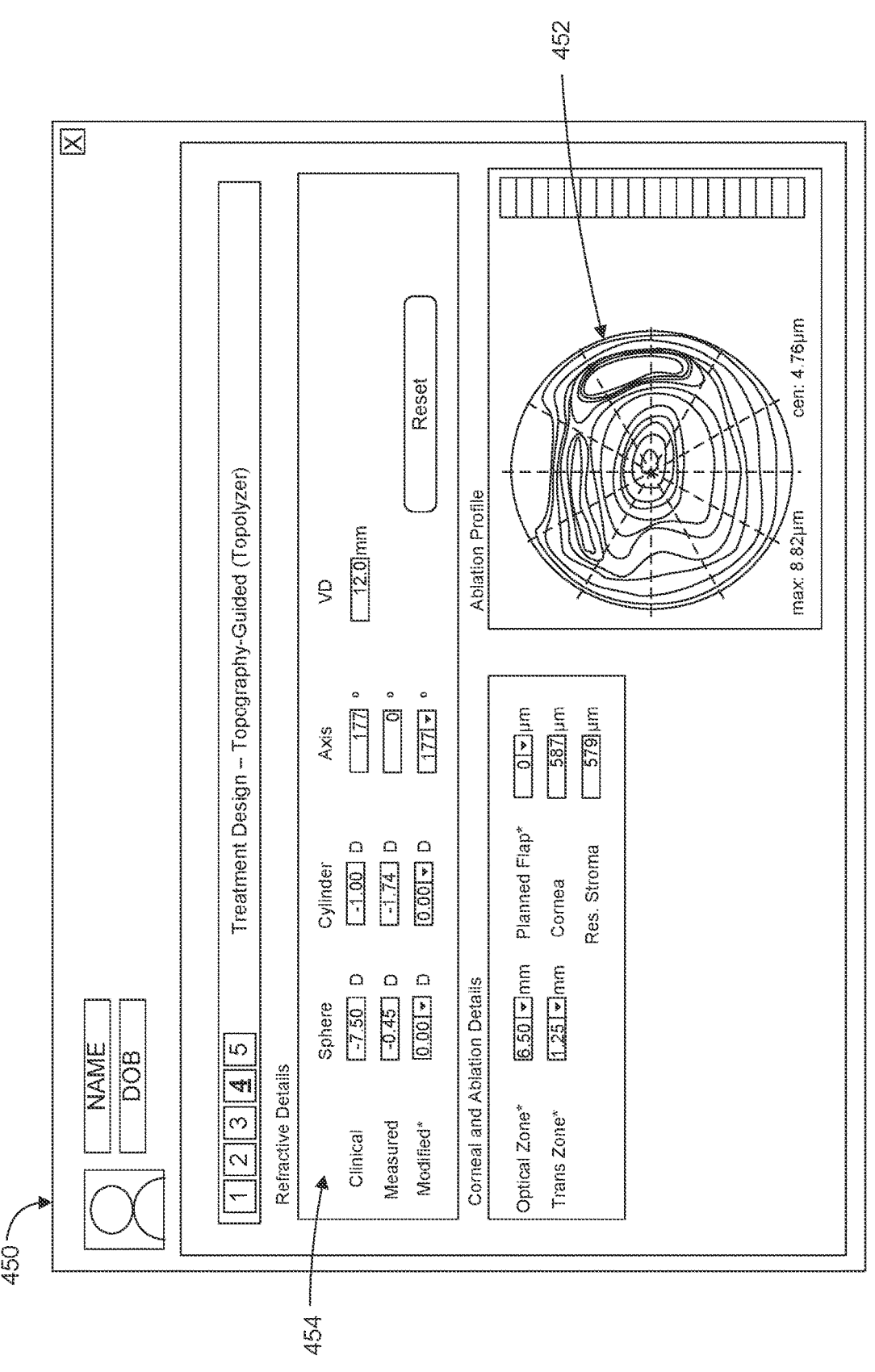
FIG. 4C depicts an example data sheet generated via Contoura® topography guided LASIK software for being uploaded into an input analyzer of an intelligent advisor system, according to one or more embodiments of the disclosure.

In various embodiments, the method 404 includes, at operation 408, uploading a corneal topography image to the system 304 for analysis by the input analyzer 316. In such embodiments, a user can upload one or more digital images into the system that include a contoured topographic image, as described above with reference to FIG. 5A. In one or more embodiments, the digital image can be in a variety of formats and include variety of information along with the topographic image. For example, in some embodiments the digital image could be of a patient data sheet generated by a known topographic imaging devices/excimer laser treatment systems. For example, an example data sheet 450 is depicted in FIG. 4C generated via Contoura® topography guided LASIK software that could be uploaded to the input analyzer. This data sheet 450 depicts a topographic image 452 and various other patient data including refractive details 454 of sphere, cylinder, axis, max, cen, and various other information.

Depicted, in FIG. 4B, in various embodiments, to upload a corneal topography image a user can access the GUI element 424 representation of the input analyzer 316 and utilize an "open image" portion 426 of the GUI 424 and upload the example data sheet 450 as a digital image file into the system 304 via an "open image" icon 428.

In various embodiments, the method 404 includes, at operation 412, inputting patient and topography data into to the system for analysis by the input analyzer 316. For example, in one or more embodiments, the refractive details 454 including, sphere, cylinder, and axis measurements can be entered into the open image portion 46 of the GUI 424. Similarly, additional information can be entered into a "patient data" portion 430 of the GUI 424 including patient eye, manifest refraction, topographic measured treatment, flat axis, steep axis, tissue ablation maximum and minimum, and other information. In various embodiments, this information is manually entered into the input analyzer 316 via the GUI 424. However, in one or more embodiments, the system 304 can be configured to automatically identify and enter various information into the system. For example in various embodiments the sphere, cylinder, and axis, or other information included in the uploaded data sheet 450 could be automatically entered into the system 304 via optical character information capabilities.

In various embodiments, the method 404 includes, at operations 416 and 420, processing the uploaded corneal topographic map using a Geographic Imaging System (GIS) and/or color or contour analyzers determining topographic vectors from the GIS processed topographic map. Topographic images contain embedded data—for instance the shape and elevation of the corneal surface—that is typically discerned via visual interpretation by a user. However, in various embodiments the input analyzer 316 includes a GIS processing module 330 and optical vector identifier to identify and recognize visual characteristics of topographic images to automatically discern or otherwise interpret the embedded visual data in the topographic image.

In various embodiments, the GIS processing module 330 and optical vector identifier 334 is a collection of software tools that allow the input analyzer to, analyze topographic information. In such embodiments the GIS processing module 330 is configured to analyze the embedded topographic/ spatial data in the topographic image to produce various vector data from the GIS analyzed topographic image 450. In such embodiments, the topographic vector is determined using the measurements of the identified taluses. In various embodiments, this is done in light of optical physics/lens theory, to determine the refractive effect of each identified talus and the effect of treatment that removes the talus.

In various embodiments, once patient information has been added in operation 412, a user can progress to operation 416 via a "processor" icon 432 in a calculate treatment portion 434 of the GUI 424. In one or more embodiments, once this icon is selected, The GIS processing module 330 and/or optical vector identifier 334 is configured to automatically identify and categorize taluses present in the uploaded topographic image. In various embodiments, talus identification is governed by a plurality of parameters including the rate of change in the slope, a height differential, or other suitable parameters. In various embodiments, the parameters used to identify taluses can be modified by the user to increase or decrease the sensitivity of talus detection, for example, to include a larger or smaller number of taluses. Once identified, the user is then presented with a new GUI element 460, depicted in FIG. 4D, which shows the results of this GIS analysis.

Figure 4D:
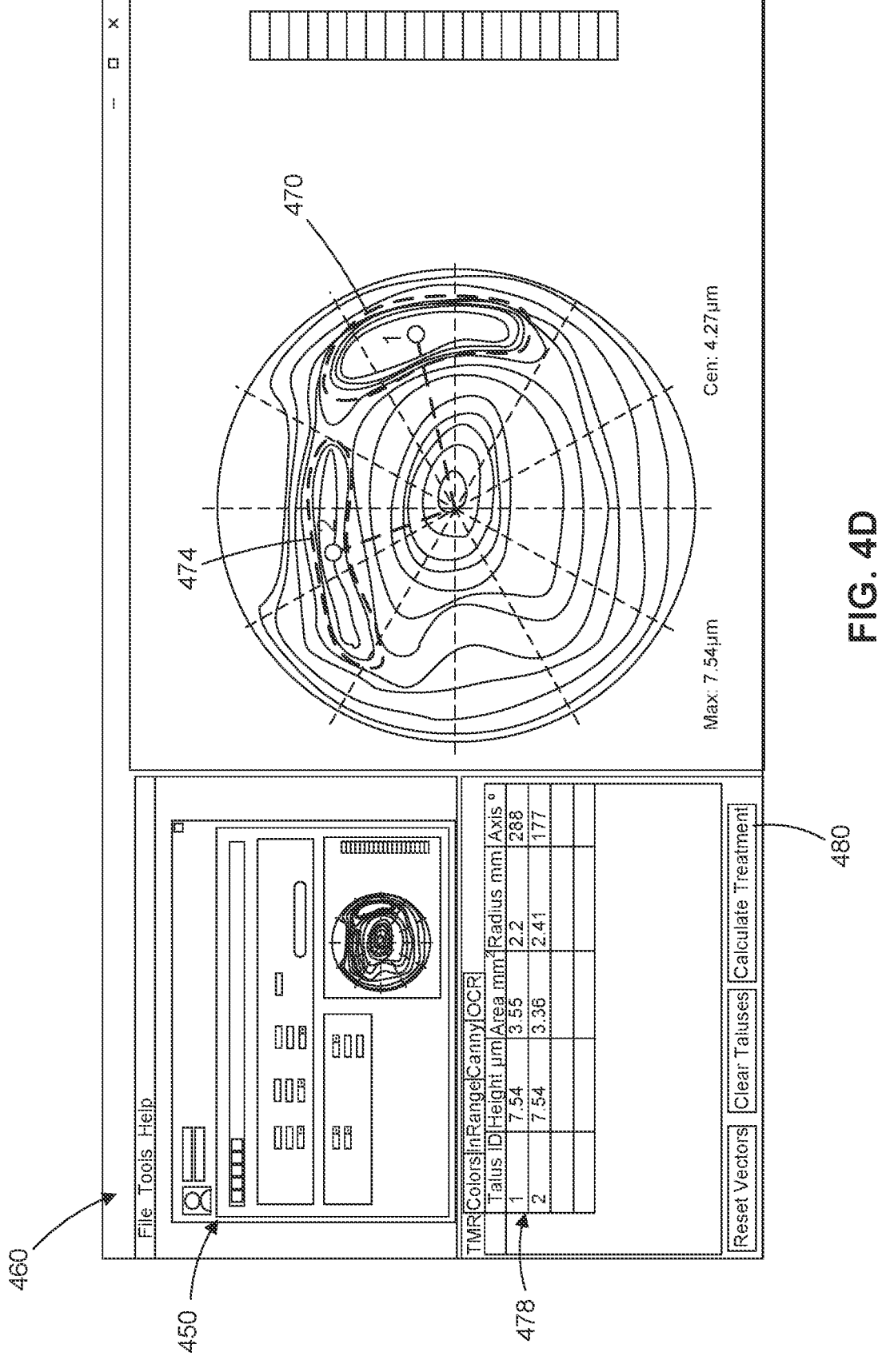
FIG. 4D depicts a GUI element representation of the results of a GIS processing module and/or optical vector identifier, according to one or more embodiments of the disclosure.

As shown in FIG. 4D the system has identified two taluses from the topographic image 450 including a first talus 470 and second talus 474, along with a determination of talus information 478 including the height, area, radius, and axis of each of the identified taluses. In various embodiments, these taluses are highlighted and labeled in the GUI 460 for easy identification by the user. In various embodiments, the input analyzer 316 additionally allows for manual identification or alteration to the automatically identified taluses.

In various embodiments, after operation 420, the method 404 concludes and the answer generator 324 of the treatment recommendation generator 310 uses the received and processed inputs to produce a treatment recommendation. In such embodiments, the answer generator 324 is a software module that uses the results/data output of the input analyzer 316 to generate a treatment recommendation. In various embodiments, the answer generator 324 can include various modules to perform analyses of received questions. For example, computer modules that answer generator 324 can encompass include, but are not limited to, a topographic analysis module 350, a cylinder compensator module 354, and a nomogram adjustment module 358.

Figure 6A:
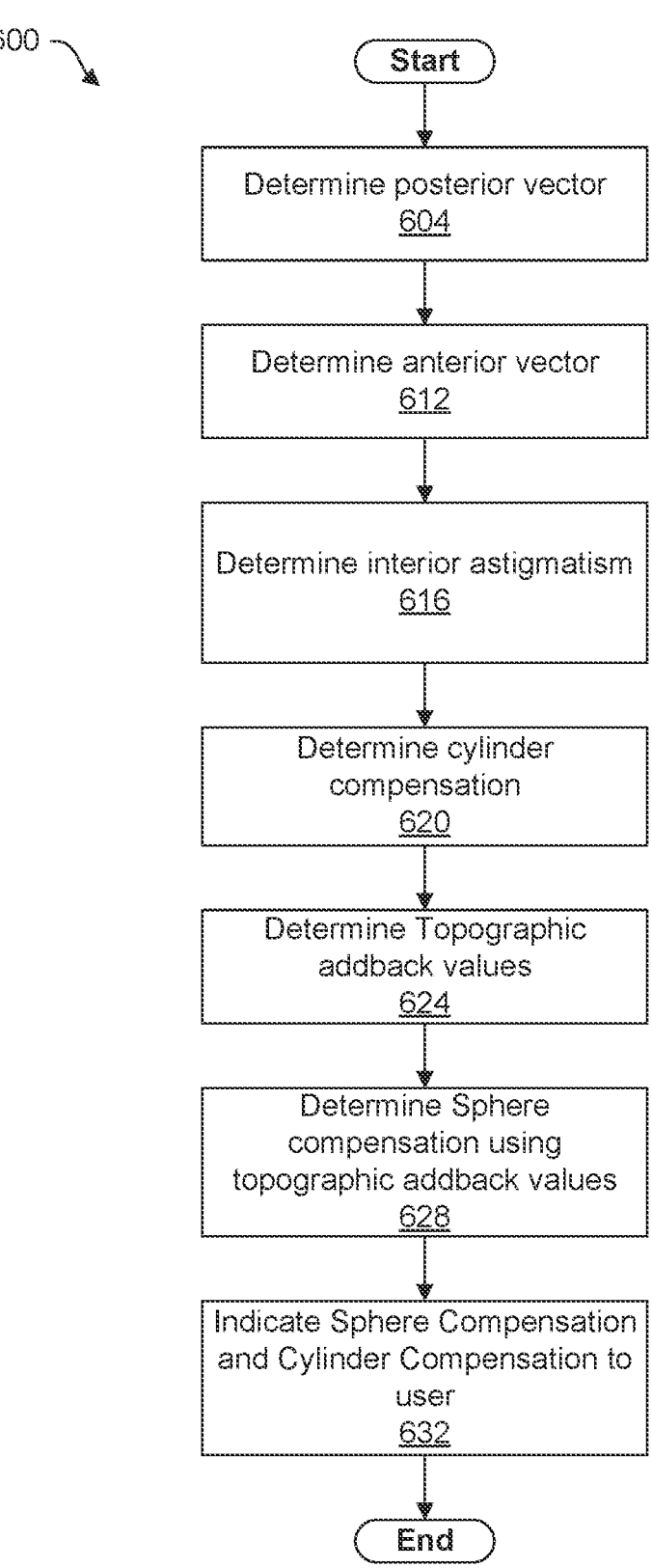
FIG. 6A depicts a flowchart diagram of a method of answer generation, according to one or more embodiments of the disclosure.
Figure 6B:
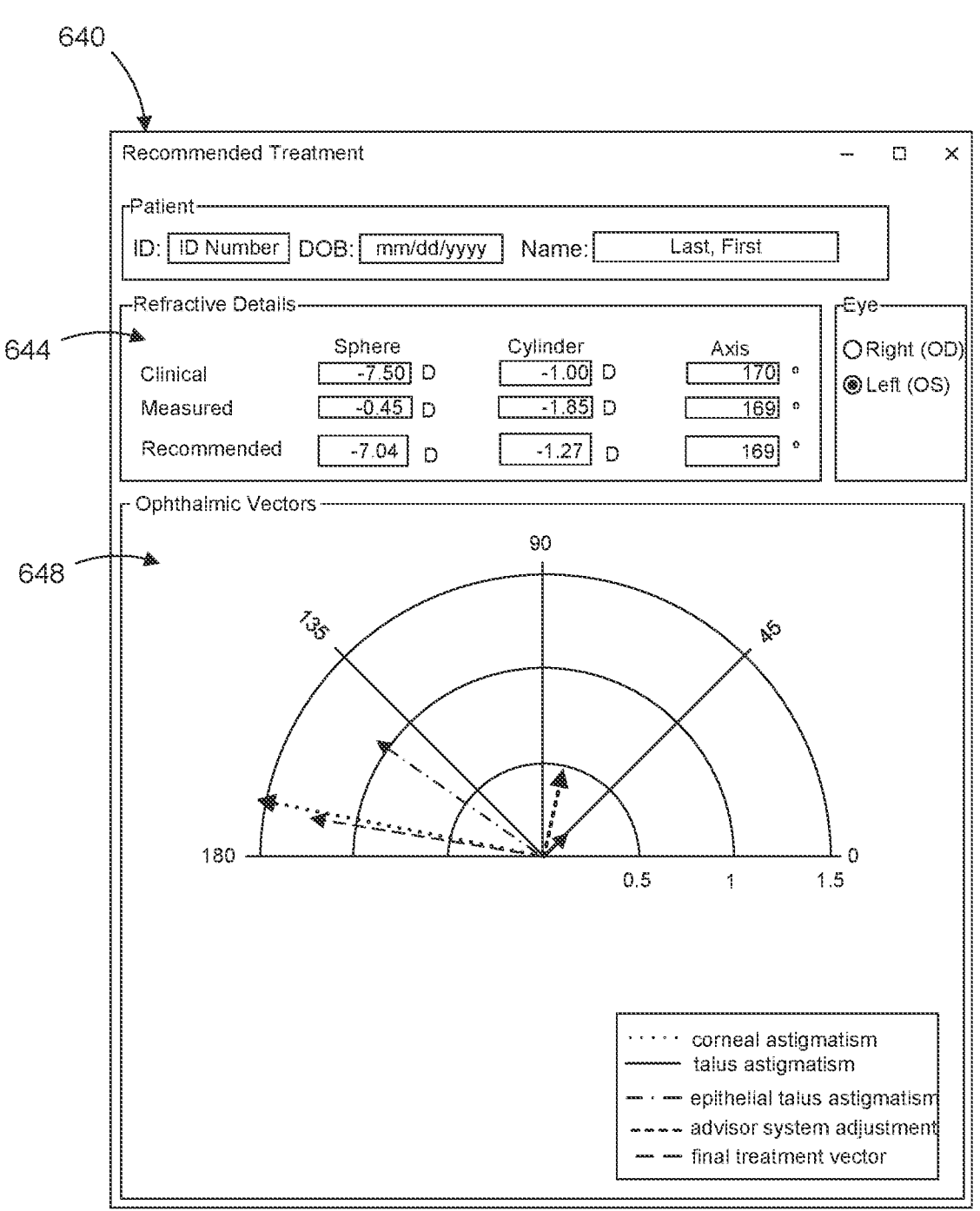
FIG. 6B-6C depicts example GUI elements of the answer generator, according to one or more embodiments of the disclosure.
Figure 6C:
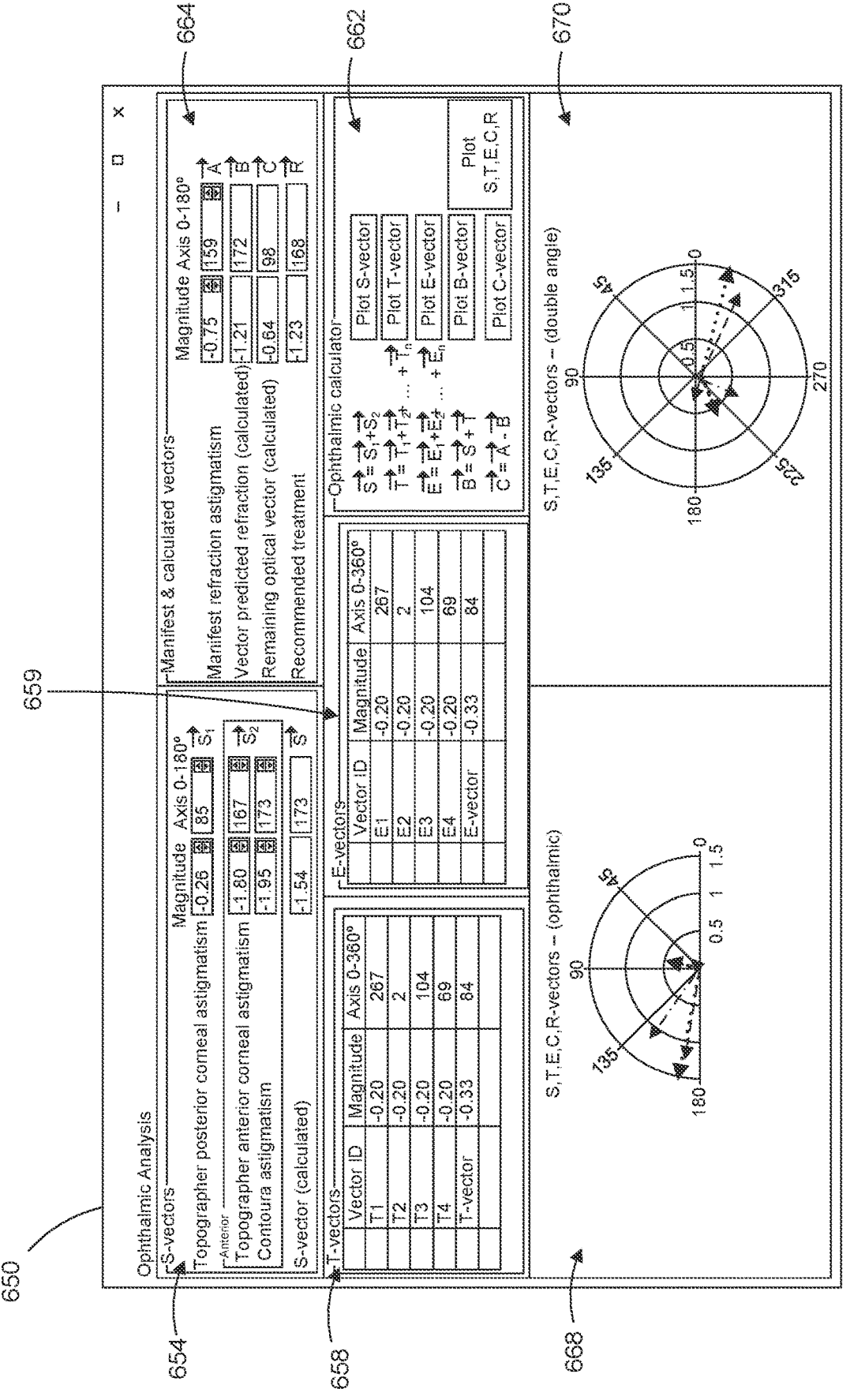

In various embodiments, a user can progress to generate a treatment recommendation via the answer generator 334 via a "calculate treatment" icon 480 in the GUI 460. Referring additionally to FIGS. 6A-6C in one or more embodiments, once this icon is selected, the topographic analysis module 350, cylinder compensator module 354, and nomogram adjustment module 358 are configured to automatically perform the various operations of method 600, described with reference to FIG. 6A, and to present the user with one or more new GUI elements, including GUI element 640 which show the recommended treatment.

Figure 4E:
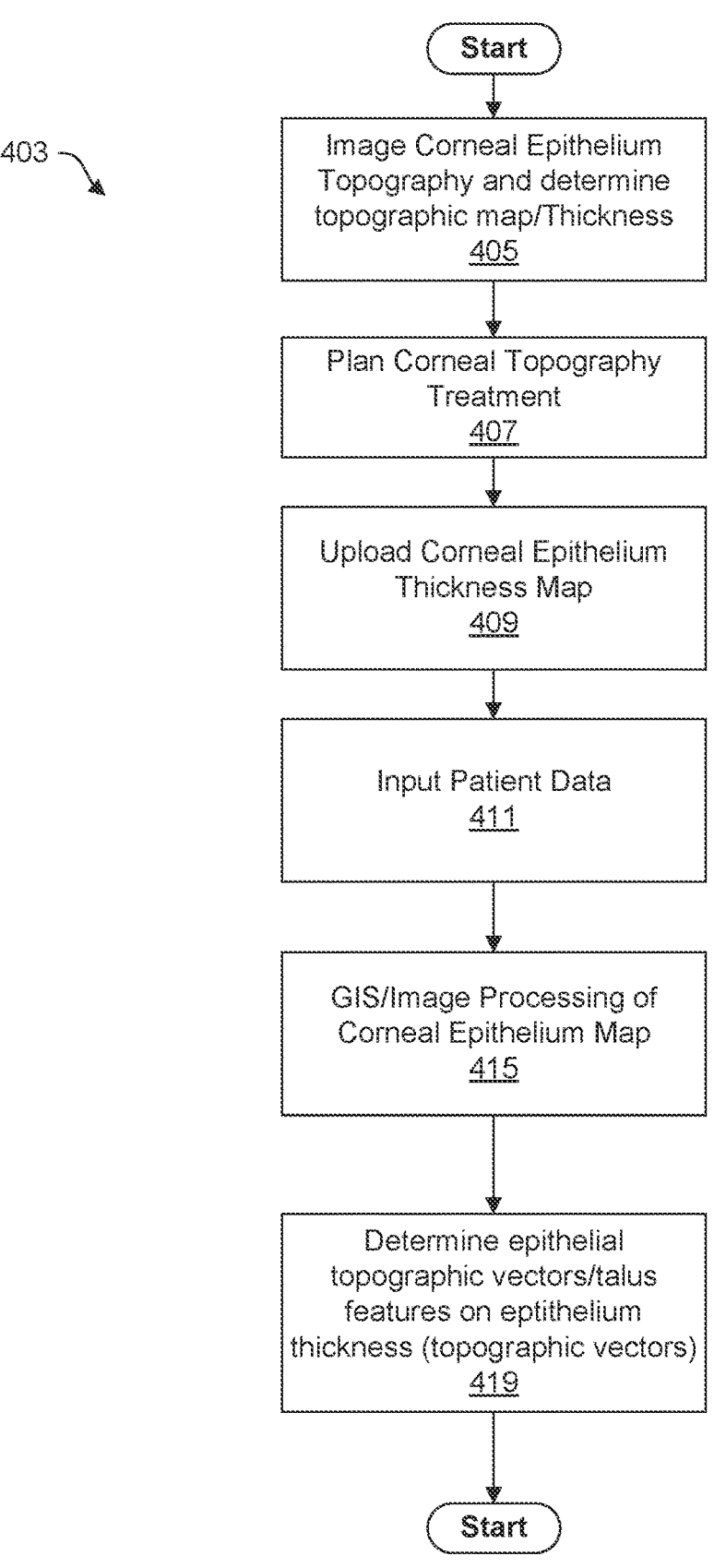
FIG. 4E depicts a flowchart diagram of a method of input analysis for an intelligent advisor system, according to one or more embodiments of the disclosure.
Figure 4F:
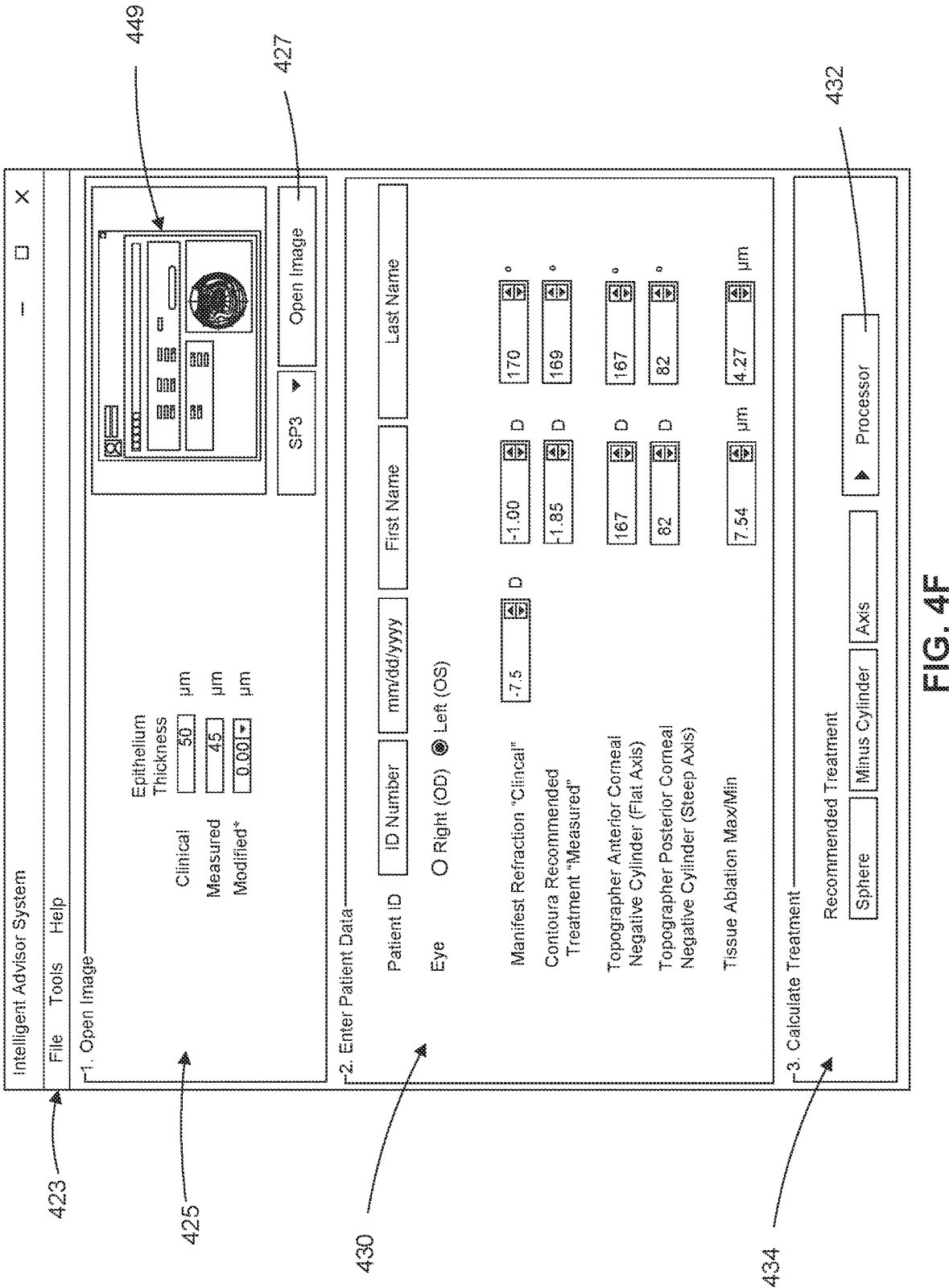
FIG. 4F depicts a GUI element of an input analyzer for an intelligent advisor system are depicted, according to one or more embodiments of the disclosure.

Referring additionally to FIGS. 4E-4F a flowchart diagram of a method 403 of input analysis and an example GUI element 423 of the input analyzer 316 are depicted, according to one or more embodiments of the disclosure. Specifically, in various embodiments, the method 403 depicts a method of operation of the input analyzer 316. As such, in one or more embodiments, and described further below, the method 403 includes various operations that can be elements of a computer program product representation of the input analyzer 316. In such embodiments, the operations of method 403 can be included as executable program instructions that are embodied in a computer readable storage medium. In various embodiments, the method 403 depicts input analyzer means for accomplishing various embodiments of the disclosure. Similarly, the GUI element 423 of FIG. 4F depict a visualization of a computer program product that, when executed by a computer, produces visual representation of the input analyzer 316.

Figure 5C:
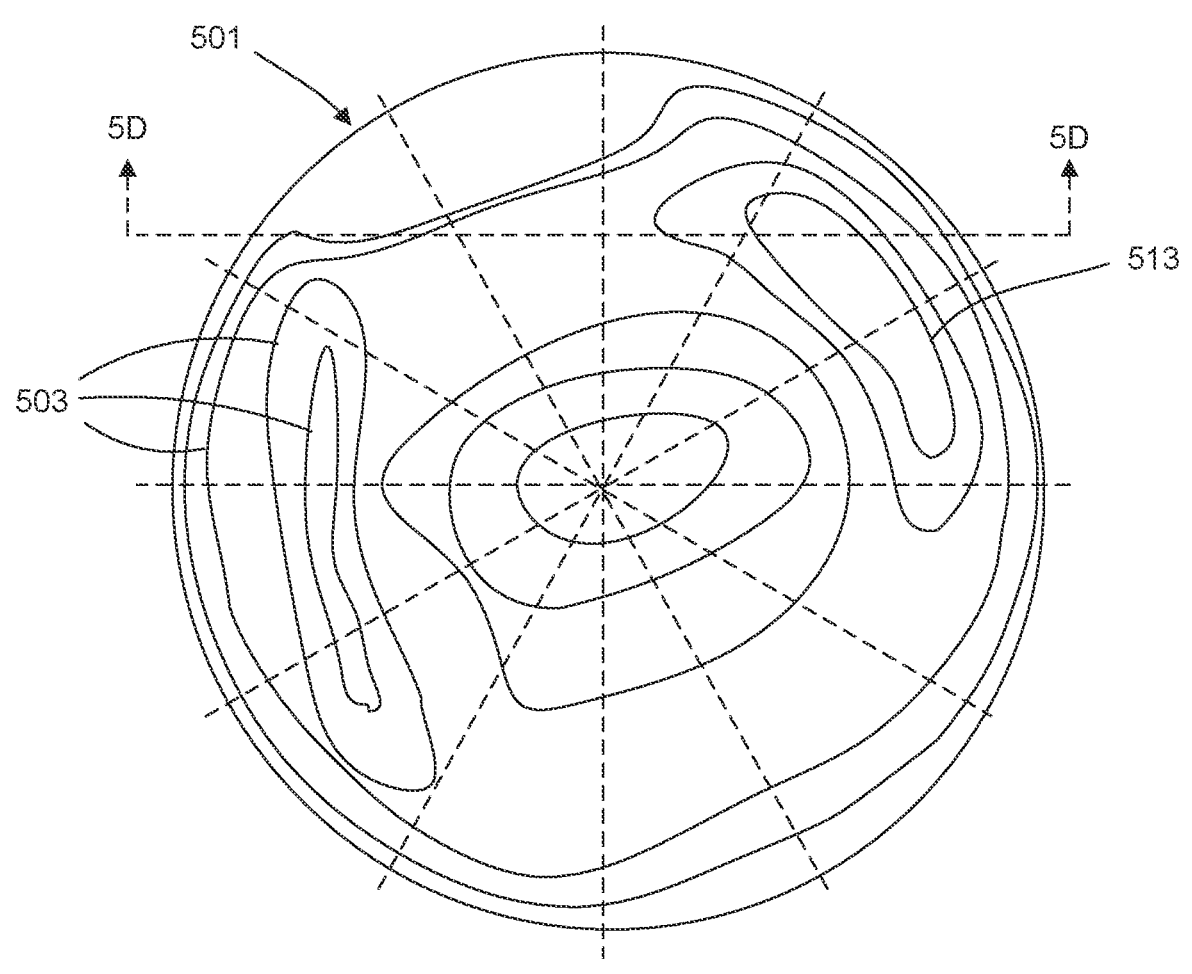
FIG. 5C depicts an epithelial thickness map of an imaged epithelium, according to one or more embodiments of the disclosure.
Figure 5D:
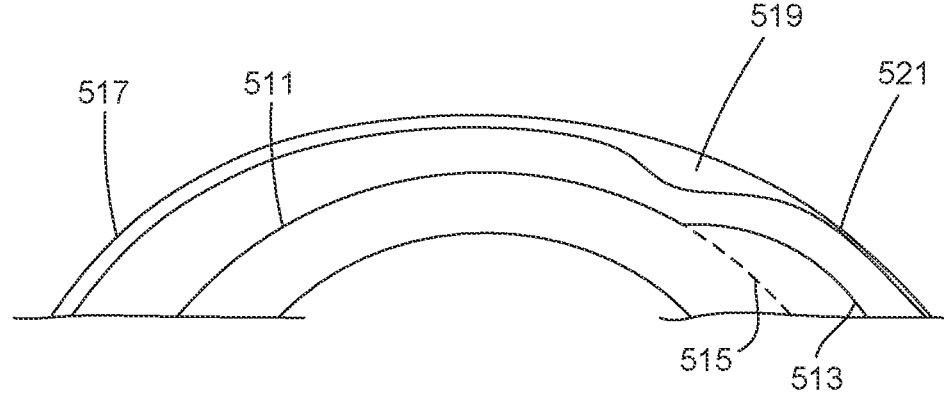
FIG. 5D depicts a partial cross-sectional view of an epithelium and cornea with a talus, according to one or more embodiments of the disclosure.

In FIG. 4E, in various embodiments, the method 403 includes, at operation 405, imaging a corneal epithelium to determine a corneal epithelial thickness and/or topographic map. As described above, corneal topography provides a detailed description of various curvature and shape characteristics of the cornea. The epithelium is the outermost layer of the cornea. Its thickness plays an important role in the overall shape and topography of the cornea. In particular, various embodiments of corneal epithelial topography and or epithelial thickness maps depict the three-dimensional shape of the cornea's surface with contour lines at specific intervals to depict the shape and thickness of the corneal epithelium layer. For example, referring to FIGS. 5C-5D, an example topographic/thickness image 501 of a corneal epithelium, a cross-sectional view of a cornea 511, and a cross-sectional view of a corneal epithelium 517 having varying thickness are depicted. As described, the topographic/thickness image 501 depicts a three-dimensional corneal epithelium layer via a plurality of contour lines 503 that depict a general shape and thickness of the corneal epithelium. As described, in various instances, the cornea 511 can include a variety of aberrations, such as an irregular shape from a portion of raised material on the corneal surface. Aberrations on cornea 511 can result in irregularities in the thickness of epithelium 517. Typically, a normal corneal epithelium has a generally uniform thickness of about 50 microns. In FIGS. 5C-5D, the cornea 511 is depicted with a collection of material formed on the side of the cornea 511 that defines a talus 513 of raised or irregular stromal material, relative to what would normally be present on a normally shaped cornea. This difference is depicted in dashed lines 515 in FIG. 5D, which depicts the material that would be present in a normal cornea and demonstrate the extent of excess material that makes up the talus 513. As described above, the talus 513 has an optical effect a patient's overall manifest refraction—potentially diminishing or negatively impacting a patient's vision. The talus 513 further has an effect on the epithelium layer 517 causing variations in thickness as the epithelium layer 517 remodels in response to shape of the corneal stroma beneath it. We have chosen to use the term "epithelial talus" to refer to such areas where the epithelium is thicker or thinner than the normal 50 microns. As shown, an elevated epithelial talus 519 or a depressed epithelial talus 521 may be located on the epithelium 517.

In various embodiments, the corneal epithelial topography and/or thickness maps can by imaged using a variety of known methods for imaging and recording a topographic image of the corneal epithelium. For example, in various embodiments epithelial thickness maps can be obtained via a Zeiss Cirrus OCT or Optovue or other suitable optical measurement device. Further, while FIG. 5C depicts an epithelial thickness map without color, in various embodiments corneal epithelial thickness maps utilize advanced color scales to identify curvature data. For example, areas of epithelial thickening can be displayed in warm colors such as red and orange, whereas areas of epithelial thinning are illustrated in cool colors such as green and blue. In various embodiments, the epithelial thickness images can be displayed according to "absolute" and/or "normalized" scales, where an absolute scaled image displays a fixed range of thicknesses and/or curvatures and the normalized scaled image displays a range of curvature or power calculated from the specific image of the cornea.

In various embodiments, the method 405 includes, at operation 407, determining a corneal topography treatment recommendation. In one or more embodiments, the images produced in operation 405 can be analyzed to develop a treatment map. In such embodiments, the treatment map will indicate the position and extent of any corneal aberrations what ablations would be required to correct the corneal shape. As described above, corneal topography treatment recommendation can be determined using one or more of a variety of standard topography based LASIK treatment systems, such as for example via Contoura® topography guided LASIK software or other suitable LASIK software. For example, referring briefly to FIG. 4C, an example treatment recommendation is depicted showing the sphere, cylinder and axis measurements, along with an ablation profile and corneal and ablation details.

In various embodiments, the method 403 includes, at operation 409, uploading a corneal epithelium thickness and/or topography image to the system 304 for analysis by the input analyzer 316. In such embodiments, a user can upload one or more digital images into the system that include a contoured epithelial thickness map and/or topographic image, as described above with reference to FIG. 5C. In one or more embodiments, the digital image can be in a variety of formats and include variety of information along with the epithelial thickness map or topographic image. For example, in some embodiments the digital image could be of a patient data sheet generated by a known topographic imaging devices/excimer laser treatment systems. For example, an example data sheet 450 is depicted in FIG. 4C generated via Contoura® topography guided LASIK software that could be uploaded to the input analyzer. This data sheet 450 depicts a topographic image 452 and various other patient data including refractive details 454 of sphere, cylinder, axis, max, cen, and various other information.

Depicted, in FIG. 4F, in various embodiments, to upload a corneal epithelial thickness map and/or topography image a user can access the GUI element 423 representation of the input analyzer 316 and utilize an "open image" portion 425 of the GUI 423 and upload an example data sheet 449 as a digital image file into the system 304 via an "open image" icon 427.

In various embodiments, the method 403 includes, at operation 411, inputting patient and topography data and epithelial thickness maps into to the system for analysis by the input analyzer 316. For example, in one or more embodiments, the refractive details 454 including, sphere, cylinder, and axis measurements can be entered into the open image portion 46 of the GUI 424. Similarly, additional information can be entered into a "patient data" portion 430 of the GUI 424 including patient eye, manifest refraction, topographic measured treatment, flat axis, steep axis, tissue ablation maximum and minimum, and other information. In various embodiments, this information is manually entered into the input analyzer 316 via the GUI 424. However, in one or more embodiments, the system 304 can be configured to automatically identify and enter various information into the system. For example in various embodiments the sphere, cylinder, and axis, or other information included in the uploaded data sheet 450 could be automatically entered into the system 304 via optical character information capabilities or by pulling such information from data stored as a CSV file as one example.

In various embodiments, the method 403 includes, at operations 415 and 419, processing the uploaded corneal epithelial thickness and/or topographic map using a Geographic Imaging System (GIS) or color or shape analyzers and determining epithelial thickness topographic refractive vectors from the GIS processed topographic map or color scales. Topographic images contain embedded data—for instance the shape and thickness of the corneal epithelial surface—that is typically discerned via visual interpretation by a user. However, in various embodiments the input analyzer 316 includes a GIS processing module 330 and optical vector identifier to identify and recognize visual characteristics of topographic images to automatically discern or otherwise interpret the embedded visual data in the topographic image.

In various embodiments, the GIS processing module 330 and optical vector identifier 334 is a collection of software tools that allow the input analyzer to, analyze topographic information. In such embodiments the GIS processing module 330 is configured to analyze the embedded topographic/spatial data in the topographic image to produce various vector data from the GIS analyzed topographic image 450. In such embodiments, the topographic vector is determined using the measurements of the identified epithelial thickness taluses. In various embodiments, this is done in light of optical physics/lens theory, to determine the refractive effect of each identified talus and the effect of treatment that removes the talus.

In various embodiments, once patient information has been added in operation 411, a user can progress to operation 416 via a "processor" icon 432 in a calculate treatment portion 434 of the GUI 424. In one or more embodiments, once this icon is selected, The GIS processing module 330 and/or optical vector identifier 334 is configured to automatically identify and categorize taluses present in the uploaded topographic and/or epithelial thickness image. In various embodiments, epithelial talus identification is governed by a plurality of parameters including the rate of change in the slope, a thickness differential, radius to the corneal center, area, or other suitable parameters. In various embodiments, the parameters used to identify epithelial taluses can be modified by the user to increase or decrease the sensitivity of epithelial talus detection, for example, to include a larger or smaller number of epithelial taluses. Once identified, the user is then presented with a new GUI element 460, depicted in FIG. 4D, which shows the results of this GIS analysis.

Figure 4G:
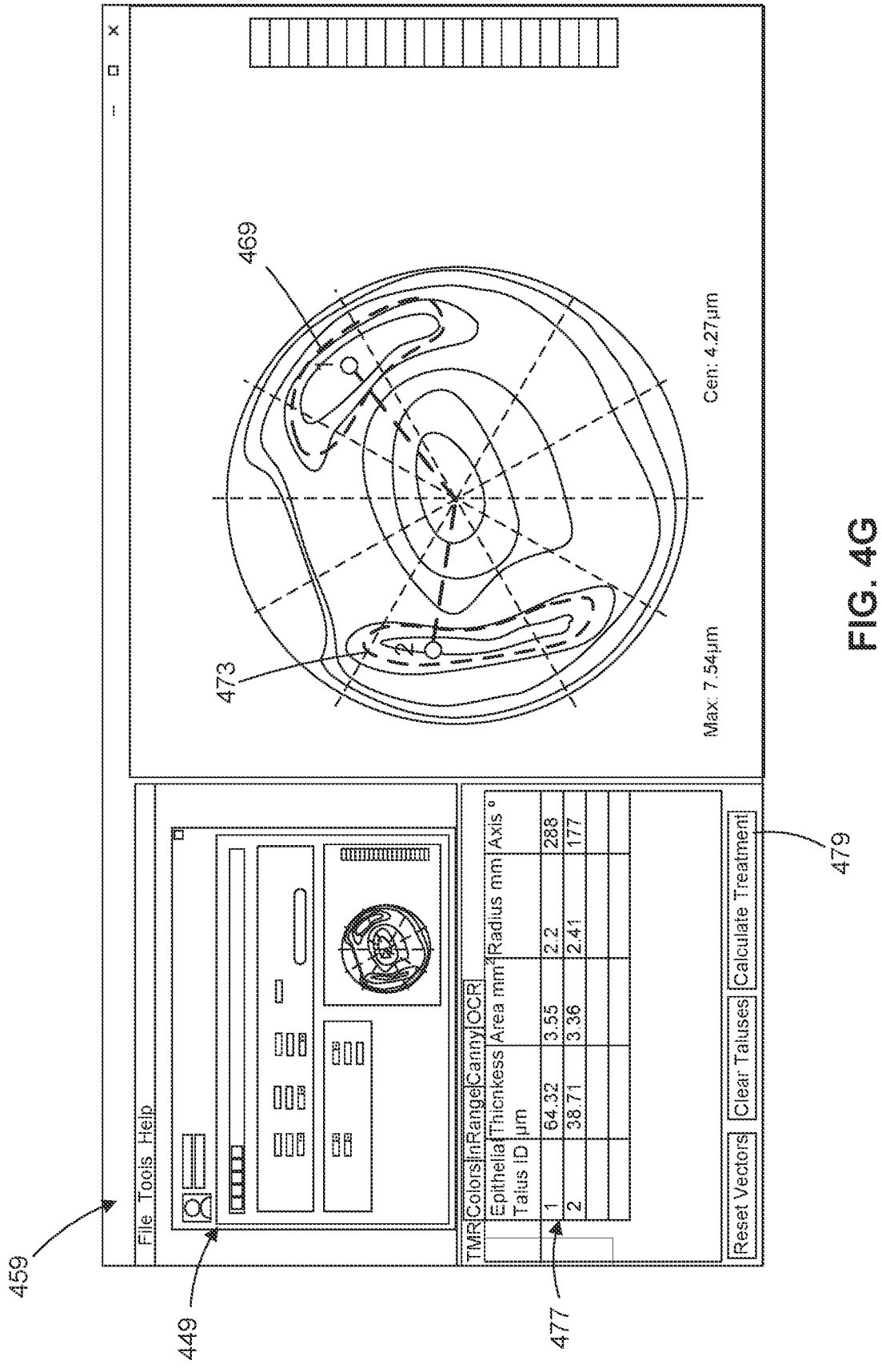
FIG. 4G depicts a GUI element representation of the results of a GIS processing module and/or optical vector identifier for an epithelial talus, according to one or more embodiments of the disclosure.

As shown in FIG. 4G the system has identified two epithelial taluses from the epithelial thickness map image 449 including a first epithelial talus 469 and second epithelial talus 473, along with a determination of epithelial talus information 477 including the thickness, area, radius, and axis of each of the identified epithelial taluses. In various embodiments, these epithelial taluses are highlighted and labeled in the GUI 459 for easy identification by the user. In various embodiments, the input analyzer 316 additionally allows for manual identification or alteration to the automatically identified taluses.

In various embodiments, after operation 419, the method 403 concludes and the answer generator 324 of the treatment recommendation generator 310 uses the received and processed inputs to produce a treatment recommendation. In such embodiments, the answer generator 324 is a software module that uses the results/data output of the input analyzer 316 to generate a treatment recommendation. In various embodiments, the answer generator 324 can include various modules to perform analyses of received questions. For example, computer modules that answer generator 324 can encompass include, but are not limited to, a topographic analysis module 350, a cylinder compensator module 354, and a nomogram adjustment module 358.

In various embodiments, a user can progress to generate a treatment recommendation via the answer generator 334 via a "calculate treatment" icon 479 in the GUI 459. Referring additionally to FIGS. 6A-6C in one or more embodiments, once this icon is selected, the topographic analysis module 350, cylinder compensator module 354, and nomogram adjustment module 358 are configured to automatically perform the various operations of method 600, described with reference to FIG. 6A, and to present the user with one or more new GUI elements, including GUI element 640 which show the recommended treatment.

In FIGS. 6A-6C a flowchart diagram of a method 600 of answer generation and an example GUI elements of the answer generator 324 are depicted, according to one or more embodiments of the disclosure. Specifically, in various embodiments, the method 600 depicts a method of operation for the answer generator 324. In such embodiments, the answer generator 324 is configured to take the processed inputs, as described above with reference to methods 403, 404, or combinations thereof, and FIGS. 4A-4F, and produce a treatment recommendation as an output for a system user. In one or more embodiments, and described further below, the method 600 includes various operations that can be elements of a computer program product representation of the answer generator 324. In such embodiments, the operations of method 600 can be included as executable program instructions that are embodied in a computer readable storage medium. As such, in various embodiments, the method 600 depicts answer generation means for accomplishing various embodiments of the disclosure. Similarly, GUI elements of FIG. 6B depict a visualization of a computer program product that, when executed by a computer, produces visual representation of the answer generator 324.

In FIG. 6A, in various embodiments, the method 600 includes, at operations 604-612, determining a posterior corneal vector and determining an anterior corneal vector. In various embodiments, this data is determined as part of the input data received and processed by the input analyzer 316. As such, in various embodiments, the posterior and anterior corneal vectors are determined in advance or in real time using standard measurement techniques, such as for example, using a Scheimpflug device that measures the posterior corneal astigmatism and/or determined using topographic analysis, such as using the Contoura® topography guided LASIK software or other LASIK topographic system. For example, referring briefly to FIG. 4B-4C, the anterior corneal vector is presented in the "refractive details" portion as the "measured" treatment design (e.g. including the magnitude and direction of the anterior astigmatism vector. Similarly, the patient data portion 430 and open image portion 426 of the GUI 424 presents the anterior corneal vector topographer anterior corneal negative cylinder and topographer posterior corneal negative cylinder as anterior and posterior astigmatism vectors determined via topographic imaging and analysis.

In various embodiments, the method 600 includes, at operation 616, determining an interior astigmatism. While not typically measurable, various embodiments of the disclosure are capable of determining the internal astigmatism via a series of vector calculations utilizing the topographic, anterior, and posterior optical vectors determined above. Described further below, various embodiments utilize vector combination and subtraction to subtract all the other vectors that are known to arrive at the internal astigmatism vector.

For instance, various embodiments arrive at the internal astigmatism vector via a vector subtraction function represented by the equation:

$$C=A-B;$$

Where C is the internal astigmatism vector, A is a manifest refraction astigmatism vector, and B is a predicted refraction vector based on talus and corneal optics. In such embodiments, the predicted refraction vector B is determined via a vector addition function represented by the equation:

$$B=S+T;$$

Where S is a total corneal astigmatism vector and T is Total complete talus vector=T determined via vector addition of all individual talus vectors, S and T determined via vector addition functions represented by the equations:

$$S=S_1(C)+S_2; \text{ and}$$

$$T=T_1+T_2+T_3 \ldots T_n;$$

Where $S_1$ is the posterior corneal astigmatism vector, C is a constant applied to modify the effect of the posterior corneal astigmatism in relation to the anterior corneal astigmatism, $S_2$ is the anterior corneal astigmatism vector, and $T_1$ through $T_n$ is each of the individual talus vectors, where n is an integer greater than 0.

In various embodiments, the predicted refraction vector B may additionally be modified by the epithelial talus vector E as determined via a vector addition function represented by the equation:

$$B=S+T+E;$$

Where E is a total complete epithelial talus vector determined via vector addition of all individual epithelial talus vectors represented by the equation:

$$E=E_1+E_2+E_3 \ldots E_n;$$

Where $E_1$ through $E_n$ is each of the individual epithelial talus vectors, where n is an integer greater than 0.

In various embodiments, C is a constant that is less than 1 such the constant C is configured to reduce the amount of effect of the posterior cornea by multiplying it by the constant C. Referring to FIG. 6C, an example GUI 650 for optical vector determination is depicted, according to one or more embodiments. In various embodiments, the GUI includes a plurality of GUI portions including a total corneal astigmatism portion 654, a talus vector portion 658, an epithelial talus portion 659, and an ophthalmic calculator portion 662. In one or more embodiments, the total corneal astigmatism portion 654 lists the posterior corneal astigmatism vector and anterior corneal astigmatism vector, while the talus vector portion 658 lists the identified talus vectors, and the epithelial talus vector portion 659 lists the identified epithelial talus vectors described above, with reference to operations 604-612 in FIG. 6A and operation 420 of FIG. 4A and operation 419 of FIG. 4E. In various embodiments, the system utilizes this data, according to the vector functions described above to arrive at the internal astigmatism vector C. The manifest and calculated vectors are presented numerically and visually in the GUI 650 at portions 664, 668, and 670.

By including the topographic vectors, for example generated above in operations 419 or 420 in method 404 of FIG. 4A and method 403 of FIG. 4E, the method 600 produces an interior astigmatism vector that is much more accurate than typical methods of determining interior astigmatism. Once obtained, the answer generator 324 is capable of determining extremely accurate predictions for what astigmatic magnitude and axis should be treated. For example, assigning a vector 90 degrees away from an epithelial talus can account for the refractive effect of the talus.

In various embodiments, the method 600 includes, at operation 620, determining a cylinder compensation—indicating a recommended anterior corneal astigmatism treatment. In one or more embodiments, due to the nature of excimer laser treatments, the shape of the anterior corneal surface will be altered as topographic features/talus are removed from the corneal surface. For instance, as a result of laser treatments the anterior surface features of the cornea will be gone while the posterior and internal astigmatism features will remain. In one or more procedures, the epithelium, which has topographic features/epithelial talus corresponding to corneal talus, is fully removed and regrows naturally following the procedure. When the epithelium regrows over the reshaped cornea, the epithelium regrows with a generally uniform thickness having different refractive characteristics than the old, removed layer. These facts are problematic for traditional excimer laser surgical systems, as the internal and posterior corneal astigmatism will remain unchanged—being unexposed to laser treatments. Traditional excimer laser surgical systems do not account for the effect of the unchanged features.

However, at operation 620, the method 600 includes calculating a cylinder compensation indicating a recommended anterior corneal astigmatism treatment that accounts for the unchanged features. In certain embodiments the cylinder compensation is calculated via a weighted combination of the C, S, A, and B vectors. For instance, various embodiments arrive at the cylinder compensation vector via a weighted combination represented by the equation:

$$R=S+0.6C;$$

Where R is the cylinder compensation vector (e.g. a recommended treatment). However, in various embodiments, if the angle of the R vector is >10 degrees away from the S-vector axis use: R-vector magnitude, S-vector axis for final treatment recommendation. If the difference between the R-vector axis and the S-vector axis is 10 degrees or less use: R-vector magnitude, R-vector axis for final treatment recommendation.

The result is a magnitude and axis that supplies a practitioner with a modified treatment for the anterior corneal astigmatism that counterbalances the unchanged interior and posterior features.

In various embodiments, the method 600 includes, at operation 624, determining a plurality of topographic addback values, and, at operation 628, determining a sphere compensation using the plurality of topographic addback values. While surgeons have found the choice of astigmatic treatment to be the most vexing problem, it is also critical to determine the correct spherical correction. To address this, in various embodiments the answer generator utilizes one or more modifiers for the spherical treatment including one or more topographic modifiers, a cylinder modifier, and a nomogram modifier.

In various embodiments, the topographic modifier is the topographic effect on the sphere. For example, if you look at the purely topographic treatment map for an eye there is often more tissue that will be ablated in the periphery of the cornea than in the center. This is depicted above, in at least FIGS. 5A-5B where ablations would occur around the periphery of the corneal surface to remove talus 512. Since this peripheral tissue removal creates an effect similar to a hyperopic spherical treatment, its effect on the sphere must be considered. In various embodiments, the answer generator utilizes at least two data pieces are entered in for this adjustment: MAX (highest talus in microns) and the CENTER (amount of tissue removed from the center). In various embodiments, the answer generator 334 is configured to calculate the difference between these two and assign a refractive value to that difference. As such, the difference between MAX and CENTER is represented by the equation:

$$Z = MAX - CENTER;$$

In various embodiments, if $Z < 5$ microns, the answer generator 334 is configured to assign a refractive value of $-0.1$ to that difference Z. In further embodiments, if $Z > 5$ microns but $< 15$ microns the answer generator 334 is configured to assign a refractive value of $-0.15$ to that difference Z. In still further embodiments, if $Z > 15$ microns the answer generator 334 is configured to assign a refractive value of $-0.2$ to that difference. In such embodiments, the refractive value to that difference is then added to the sphere as the topographic modifier.

In various embodiments where the epithelium layer is fully removed, the answer generator 334 is configured to adjust 1 diopter of refractive sphere for each 15.9 microns of stromal tissue ablated. The answer generation 334 may calculate the delta, or deviation, from the 50 micron standard thickness. For example, consider a circular region of the central cornea that measures an epithelial depth of 60 microns. Answer generator 334 will determine a delta of 10 microns by subtracting the standard 50 micron thickness from the measured depth of 60 microns. Answer generator 314 then divides the delta of 10 microns by 15.9 to determine a change of 0.63 diopters. If the patient's manifest sphere was $-5.00$ diopters, the treatment recommended would be $-4.37$. A failure to account for the epithelium regrowing to 50 microns, a 10 micron loss of total corneal elevation as compared to pre-operative measurements, would result in over-correction and $+0.063$ diopters of hyperopia.

In various embodiments, the cylinder modifier value is determined by calculating a difference between the magnitude of the patient's manifest astigmatism and the magnitude of the astigmatism that will be treated. Once calculated, in various embodiments the system will take $\frac{1}{2}$ this difference and add it back to the sphere to maintain the patient's spherical equivalency. For example, in a hypothetical example where the manifest astigmatism is $-0.75$ D and the measured astigmatism is $-1.74$ D. If one was to treat based off of the measured astigmatism there is a $-0.99$ difference. In such instances, the cylinder modifier value would be $\frac{1}{2} \times -0.99$ or $-0.495$ D. In various embodiments, since we have increased the minus cylinder we must add this back as a + to the sphere, so $+0.495$ would be added to the sphere to maintain spherical equivalency.

In one or more embodiments, the nomogram adjustment is a final adjustment to the sphere based on a best-fit regression model of achieved correction versus attempted correction for patients having similar pre-operative refraction data. In such embodiments, the nomogram adjustment is formulated using a large number of post-operative results to create a best fit line using regression analysis. In such embodiments, the nomogram adjustment is calculated by using the best-fit regression model to identify the predicted sphere adjustment for each patient. While in certain embodiments the nomogram adjustment is calculated using a best-fit regression model, any predictive modeling means can be used to create a nomogram adjustment. For example, in certain embodiments a large number of results could be seeded through a deep learning/pattern recognition to identify patterns/corrections to develop a nomogram adjustment. In such embodiments, the advisor system can collect results from individualized practitioners and create a personalized nomogram for each individual surgeon further improving the accuracy.

In various embodiments, the method 600 includes, at operation 632, indicating the sphere compensation and cylinder compensation to a user. In various embodiments, these compensation values are indicated via a GUI or other display to indicate an advised ablation profile for a patent.

For example, referring to FIG. 6B, the GUI element 640 of the answer generator 324 is indicates a variety of ablation profiles, including a system generated recommended treatment or treatment recommendation in a "refractive details" portion 640 of the GUI. Specifically, recommended treatment details sphere, cylinder, and axis treatments for the ablation profile calculated based on the process described herein with reference to methods 404 and 600. However, in various embodiments and as depicted in GUI element 640, the refractive details portion 644 additionally displays the clinical and measured results. In such embodiments, the system provides additional information to the practitioner along with the recommended treatment, to allow a practitioner to make an informed decision on which treatment to take and/or to modify the treatment. In various embodiments, the GUI element 640 can additionally include a visual indication of a plurality of optical vectors. For example, the GUI element 640 includes an "ophthalmic vector" portion 648 including a vector graph showing the corneal astigmatism, talus astigmatism, advisor system adjustment, and a final treatment vector.

In various embodiments, the vector diagram can assist a user in explaining why the system recommends a generated cylinder compensation and spherical compensation values that potentially differs from the measured or input values. For example, in addition to the above described and discussed, Appendices A-F, included herewith and incorporated by reference herein for all purposes, depict examples of producing a recommended treatment, and how the vector diagram indicates or explains the generated values to a practitioner in a variety of scenarios. In addition, these appendices depict a variety of examples of the process 600, according to embodiments of the disclosure.

In addition, while the various embodiments described herein are directed for a system for providing intelligent advice in astigmatic calculations for LASIK treatments, it can also be used for other fields, such as other ophthalmic treatments that include astigmatic measurements. For example, various embodiments are applicable for SMILE, intra ocular lens calculations, and astigmatic incisions, or other similar types of ophthalmic treatments including astigmatic measurements.

Figure 7:
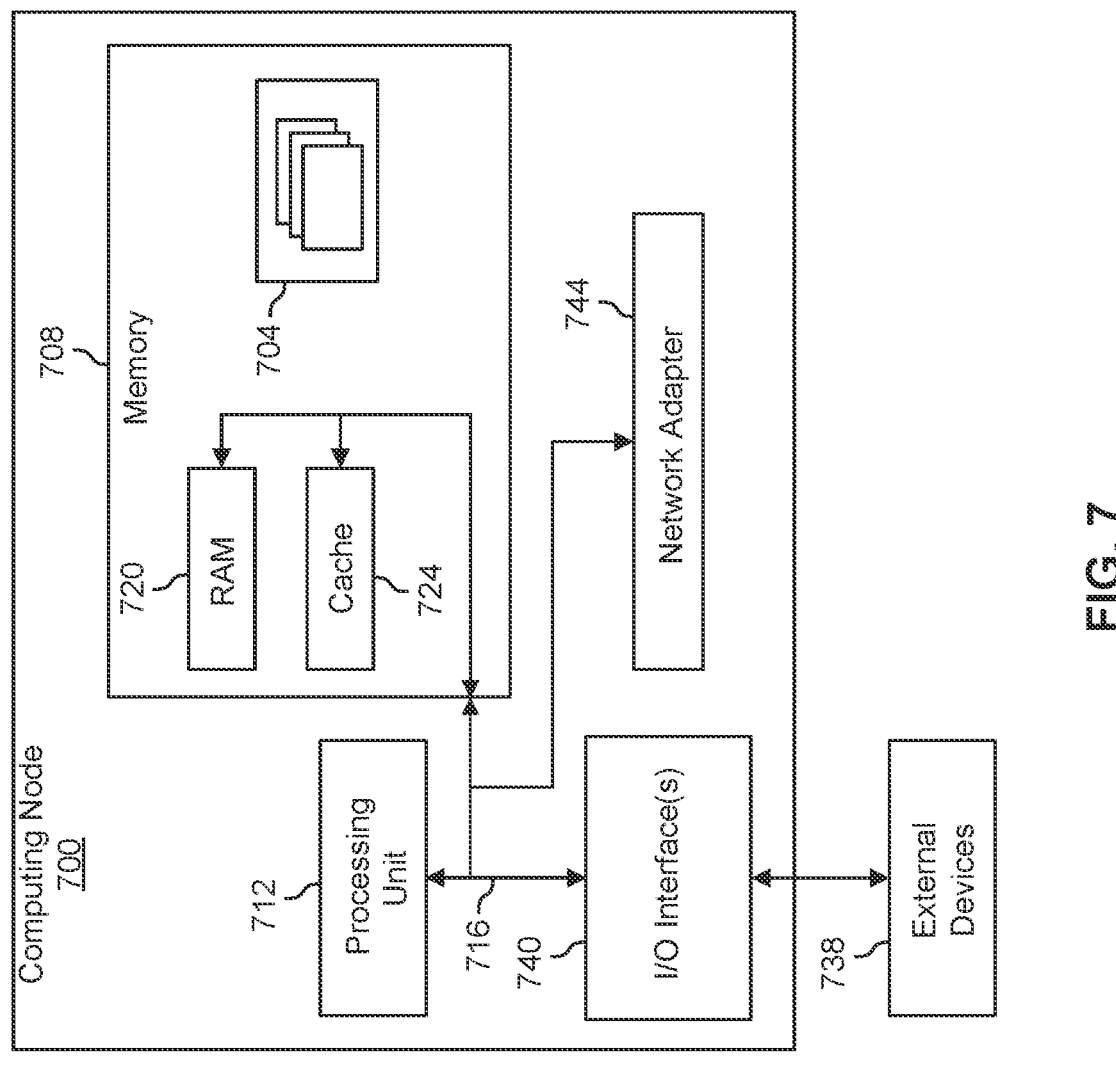
FIG. 7 depicts a computing node 700 including a processor and a computer readable storage unit, according to one or more embodiments of the disclosure.

Referring to FIG. 7, a computing node 700 including a processor and a computer readable storage unit are depicted, according to one or more embodiments of the disclosure. In various embodiments, computing node 700 is for use in intelligent advisor system for executing various embodiments of the disclosure as described above. For example, and as described herein, computing node 700 can be configured to execute and/or store various program instructions as a part of a computer program product. computing node 700 may be operational with general purpose or special purpose computing system environments or configurations, such as the intelligent advisor system described according to one or more of the embodiments herein.

Examples of computing systems, environments, and/or configurations that may be suitable for use with computing node 700 include, but are not limited to, personal computer systems, server computer systems, handheld or laptop devices, multiprocessor systems, mainframe computer systems, distributed computing environments, and the like.

Computing node 700 may be described in the general context of a computer system, including executable instructions, such as program modules 704, stored in system memory 708 being executed by a processor 712. Program modules 704 may include routines, programs, objects, instructions, logic, data structures, and so on, that perform particular tasks or implement particular abstract data types. Program modules 704 may be practiced in distributed computing environments where tasks are performed by remote processing devices that are linked through a network. In a distributed computing environment, program modules 704 may be located in both local and remote computer system storage media including memory storage devices. As such, in various embodiments computing node 700 can be configured to execute various program modules 704 or instructions for executing various embodiments of the disclosure. For example, in various embodiments computing node 700 can be configured to generate a treatment recommendation for topographic applications of excimer laser surgery.

The components of the computing node 700 may include, but are not limited to, one or more processors 712, memory 708, and a bus 716 that couples various system components, such as, for example, the memory 708 to the processor 712. Bus 716 represents one or more of any of several types of bus structures, including, but not limited to, a memory bus and/or memory controller, a peripheral bus, and a local bus using a suitable of bus architecture.

In one or more embodiments, computing node 700 includes a variety of computer readable media. In one or more embodiments, computer readable media includes both volatile and non-volatile media, removable media, and non-removable media.

Memory 708 may include computer readable media in the form of volatile memory, such as random access memory (RAM) 720 and/or cache memory 724. Computing node 700 may further include other volatile/non-volatile computer storage media such as hard disk drive, flash memory, optical drives, or other suitable volatile/non-volatile computer storage media. As described herein, memory 708 may include at least one program product having a set (e.g., at least one) of program modules 704 or instructions that are configured to carry out the functions of embodiments of the disclosure.

Computing node 700 may also communicate with one or more external devices 738 such as other computing nodes, a display, keyboard, or other I/O devices, via an I/O interface (s) 740 for transmitting and receiving sensor data, instructions, or other information to and from the computing node 700. In one or more embodiments, I/O interface 740 includes a transceiver or network adaptor 744 for wireless communication. As such, in one or more embodiments, I/O interface 740 can communicate or form networks via wireless communication.

One or more embodiments may be a computer program product. The computer program product may include a computer readable storage medium (or media) including computer readable program instructions for causing a processor to enhance target intercept according to one or more embodiments described herein.

The computer readable storage medium is a tangible device that can retain and store instructions for use by an instruction execution device. The computer readable storage medium may be, for example, an electronic storage device, a magnetic storage device, an optical storage device, or other suitable storage media.

A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Program instructions, as described herein, can be downloaded to respective computing/processing devices from a computer readable storage medium or to an external computer or external storage device via a network, for example, the Internet, a local area network, a wide area network and/or a wireless network. A network adapter card or network interface in each computing/processing device may receive computer readable program instructions from the network and forward the computer readable program instructions for storage in a computer readable storage medium within the respective computing/processing device.

Computer readable program instructions for carrying out one or more embodiments, as described herein, may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages.

The computer readable program instructions may execute entirely on a single computer, or partly on the single computer and partly on a remote computer. In some embodiments, the computer readable program instructions may execute entirely on the remote computer. In the latter scenario, the remote computer may be connected to the single computer through any type of network, including a local area network (LAN) or a wide area network (WAN), or public network.

One or more embodiments are described herein with reference to flowchart illustrations and/or block diagrams of methods, systems, and computer program products according to one or more of the embodiments described herein. It will be understood that each block of the flowchart illustrations and/or block diagrams, and combinations of blocks in the flowchart illustrations and/or block diagrams, may be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the method steps discussed above, or flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The method steps, flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some embodiments, the functions noted in the block may occur out of the order noted in the figures. For example, two blocks shown in succession may in fact, be executed substantially concurrently, or the blocks may sometimes be executed in the reverse order, depending upon the functionality involved.

In one or more embodiments, the program instructions of the computer program product are configured as an "App" or application executable on a laptop or handheld computer utilizing a general-purpose operating system. As such, in various embodiments can be implemented on a handheld device such as a tablet, smart phone, or other device.

In various embodiments, the code/algorithms for implementing one or more embodiments are elements of a computer program product, as described above, as program instructions embodied in a computer readable storage medium. As such, such code/algorithms can be referred to a program instruction means for implementing various embodiments described herein.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to explain the principles of the embodiments, the practical application or technical improvement over technologies found in the marketplace, or to enable others of ordinary skill in the art to understand the embodiments disclosed herein.

What is claimed is:

1. An intelligent advisor system for generating a treatment recommendation for corneal surgical procedures on an eye, the treatment recommendation including a cylinder compensation and a spherical compensation, the system comprising:
   a processor; and
   a computer readable storage medium having program instructions embodied therewith, wherein the computer readable storage medium is not a transitory signal per se, the program instructions executable by the processor to cause the processor to:
      determine a topographic vector from a topographic corneal map of the eye, the topographic vector indicating a magnitude and a direction of an optical effect of a corneal talus;
      determine an epithelial thickness topographic vector from a topographic corneal epithelium map of the eye, the epithelial thickness topographic vector indicating a magnitude and a direction of an optical effect of an epithelial talus;
      determine a posterior astigmatism vector and an anterior astigmatism vector for the eye;
      generate an interior astigmatism vector using the topographic vector, the epithelial thickness topographic vector, the posterior astigmatism vector, the anterior astigmatism vector, and a manifest astigmatism vector;
      generate the cylinder compensation of the treatment recommendation using the interior astigmatism vector and the posterior astigmatism vector;
      generate the spherical compensation of the treatment recommendation using an initial spherical compensation modified by a topographic addback modifier and a cylinder addback modifier;
      where the topographic addback modifier is a value indicating a combined refractive effect of a difference between a height of a highest talus and an amount of tissue removed from the center of the cornea associated with the treatment recommendation and a difference between an epithelial talus thickness and an average epithelium thickness; and
      where the cylinder addback modifier is a value of one half a difference between a magnitude of the manifest astigmatism vector and a magnitude of the cylinder compensation; and
   indicate the treatment recommendation including the cylinder compensation and the sphere compensation to a user.

2. The system of claim 1, wherein the initial spherical compensation is further modified by a nomogram addback modifier, where the nomogram addback modifier is based on a best-fit regression model of achieved correction versus attempted correction.

3. The system of claim 1, wherein the program instructions are executable by the processor to further cause the processor to:
   receive a plurality of inputs including the topographic corneal map, topographic and/or corneal epithelial thickness map, the posterior astigmatism vector, the anterior astigmatism vector, and the initial spherical compensation.

4. The system of claim 3, wherein the plurality of inputs are generated using commercially available topography guided LASIK software.

5. The system of claim 1, wherein the topographic vector is generated using GIS (geographical imaging system) processing of the topographic corneal map and the epithelial thickness topographic vector is generated using GIS processing of a topographic and/or corneal epithelial thickness map.

6. The system of claim 1, wherein the topographic vector is one of a set of one or more topographic vectors determined from the topographic corneal map of the eye, each of the set of topographic vectors indicating a magnitude and a direction of an optical effect of a corneal talus, and the epithelial vector is one of a set of one or more epithelial vectors determined from a topographic and/or corneal epithelial thickness map.

7. The system of claim 6, wherein the program instructions are executable by the processor to further cause the processor to:
   generate a predicted refraction vector based on talus and corneal optics, where the predicted refraction vector is determined via a vector addition function summing a total corneal astigmatism vector, a total talus vector, and a total epithelial talus vector, where the total corneal astigmatism vector is a vector determined via vector addition between the posterior astigmatism vector and the anterior astigmatism vector, and where the total corneal astigmatism vector is a vector determined via vector addition between each of the set of one or more topographic vectors; and wherein the interior astigmatism vector is generated using the predicted refraction vector.

8. The system of claim 7, wherein the interior astigmatism vector is a vector generated by a vector subtraction between the manifest refraction astigmatism vector and the predicted refraction vector.

9. The system of claim 1, wherein the corneal surgical procedures include a topographic-based excimer laser surgical procedure.

10. The system of claim 1, wherein the corneal surgical procedures include one or more of a PRK surgery, a SMILE surgery, astigmatic incisions, and astigmatism management for cataract surgery.

11. The system of claim 1, further comprising a corneal topographer used to generate the topographic corneal map of the eye, the corneal topographer using at least one of Scheimpflug imaging or optical coherence tomography (OCT) imaging.

12. A method for generating a cylinder compensation and a spherical compensation for a corneal surgical procedure on an eye, the method comprising:

determining a topographic vector from a topographic corneal map of the eye, the topographic vector indicating a magnitude and a direction of an optical effect of a corneal talus;

determining an epithelial topographic thickness refractive vector from an epithelial topographic/thickness corneal map of the eye, the epithelial vector indicating a magnitude and a direction of an optical effect of an epithelial talus;

determining a posterior astigmatism vector and an anterior astigmatism vector for the eye;

generating an interior astigmatism vector using the topographic vector, the epithelial topographic thickness vector, the posterior astigmatism vector, the anterior astigmatism vector, and a manifest astigmatism vector;

generating the cylinder compensation of a treatment recommendation using the interior astigmatism vector and the posterior astigmatism vector; and generating the spherical compensation of the treatment recommendation using an initial spherical compensation modified by a topographic addback modifier and a cylinder addback modifier;

where the topographic addback modifier is a value indicating a combined refractive effect of a difference between a height of a highest talus and an amount of tissue removed from the center of the cornea associated with the treatment recommendation and a difference between an epithelial talus thickness and an average epithelium thickness of 50 microns; and where the cylinder addback modifier is a value of one half a difference between a magnitude of the manifest astigmatism vector and a magnitude of the cylinder compensation.

13. The method of claim 12, wherein the initial spherical compensation is further modified by a nomogram addback modifier, where the nomogram addback modifier is based on a best-fit regression model of achieved correction versus attempted correction.

14. The method of claim 12, wherein the method further comprises:

receiving a plurality of inputs including the topographic corneal map, the epithelial topographic/thickness corneal map, the posterior astigmatism vector, the anterior astigmatism vector, and the initial spherical compensation.

15. The method of claim 14, wherein the plurality of inputs are generated using commercially available topography guided LASIK software.

16. The method of claim 12, wherein the topographic vector is generated using GIS (geographical imaging system) processing of the topographic corneal map and the epithelial topographic/thickness corneal map.

17. The method of claim 12, wherein the topographic vector is one of a set of one or more topographic vectors determined from the topographic corneal map of the eye, each of the set of topographic vectors indicating a magnitude and a direction of an optical effect of a corneal talus, and the epithelial topographic/thickness vector is one of a set of one or more epithelial topographic/thickness vectors determined from the topographic/thickness corneal epithelial map of the eye, each of the set of epithelial talus vectors indicating a magnitude and a direction of an optical effect of an epithelial talus.

18. The method of claim 17, wherein the method further comprises:

generating a predicted refraction vector based on talus, epithelial talus, and corneal optics, where the predicted refraction vector is determined via a vector addition function summing a total corneal astigmatism vector and a total talus vector, where the total corneal astigmatism vector is a vector determined via vector addition between the posterior astigmatism vector and the anterior astigmatism vector, and where the total corneal astigmatism vector is a vector determined via vector addition between each of the set of one or more topographic vectors and each of the set of one or more epithelial topographic vectors; and wherein the interior astigmatism vector is generated using the predicted refraction vector.

19. The method of claim 18, wherein the interior astigmatism vector is a vector generated by a vector subtraction between the manifest refraction astigmatism vector and the predicted refraction vector.

20. A computer program product for generating a cylinder compensation and a spherical compensation for a corneal surgical procedure on an eye wherein the computer program product is not a transitory signal per se, the computer program product comprising instructions executable by one or more processors to cause the one or more processors to perform a method comprising:

determining a topographic vector from a topographic corneal map of the eye, the topographic vector indicating a magnitude and a direction of an optical effect of a corneal talus;

determining an epithelial talus vector from a topographic/thickness corneal epithelial map of the eye, the epithelial talus vector indicating a magnitude and a direction of an optical effect of an epithelial talus;

determining a posterior astigmatism vector and an anterior astigmatism vector for the eye;

generating an interior astigmatism vector using the topographic vector, the posterior astigmatism vector, the anterior astigmatism vector, and a manifest astigmatism vector;

generating the cylinder compensation of a treatment rec-
ommendation using the interior astigmatism vector and
the posterior astigmatism vector; and generating the spherical compensation of the treatment
recommendation using an initial spherical compensa-
tion modified by a topographic addback modifier and a
cylinder addback modifier, where the topographic addback modifier is a value indi-
cating a combined refractive effect of a difference
between a height of a highest talus and an amount of
tissue removed from the center of the cornea associated
with the treatment recommendation and a difference
between an epithelial talus thickness and an average
epithelium thickness of 50 microns, and where the cylinder addback modifier is a value of one half
a difference between a magnitude of the manifest
astigmatism vector and a magnitude of the cylinder
compensation.

* * * * *